US009420952B2

(12) United States Patent
Paquet et al.

(10) Patent No.: US 9,420,952 B2
(45) Date of Patent: Aug. 23, 2016

(54) TEMPERATURE PROBE SUITABLE FOR AXILLARY READING

(75) Inventors: Pierre Paquet, Quebec (CA); Binta Diallo, Quebec (CA); Mark Raptis, Valley Center, CA (US)

(73) Assignee: CareFusion 303, Inc., San Diego, CA (US)

( * ) Notice: Subject to any disclaimer, the term of this patent is extended or adjusted under 35 U.S.C. 154(b) by 558 days.

(21) Appl. No.: 12/844,775

(22) Filed: Jul. 27, 2010

(65) Prior Publication Data
US 2012/0029310 A1 Feb. 2, 2012

(51) Int. Cl.
*A61B 5/00* (2006.01)
*A61B 5/01* (2006.01)
*A61B 5/0205* (2006.01)

(52) U.S. Cl.
CPC ............... *A61B 5/0008* (2013.01); *A61B 5/01* (2013.01); *A61B 5/02055* (2013.01); *A61B 5/6813* (2013.01); *A61B 5/6833* (2013.01); *A61B 2562/0271* (2013.01)

(58) Field of Classification Search
USPC .................................................. 600/549, 301
See application file for complete search history.

(56) References Cited

U.S. PATENT DOCUMENTS

| 3,677,261 | A |   | 7/1972  | Day            |         |
|-----------|---|---|---------|----------------|---------|
| 3,805,769 | A |   | 4/1974  | Sessions       |         |
| 3,830,224 | A | * | 8/1974  | Vanzetti et al.| 600/549 |
| 3,845,757 | A |   | 11/1974 | Weyer          |         |
| 4,121,574 | A |   | 10/1978 | Lester         |         |
| 4,396,020 | A |   | 8/1983  | Wolff et al.   |         |
| 4,407,295 | A | * | 10/1983 | Steuer ........... A61B 5/02438 600/483 |
| 4,490,005 | A |   | 12/1984 | Hovey          |         |
| 4,527,087 | A |   | 7/1985  | Taya et al.    |         |
| 4,530,366 | A |   | 7/1985  | Nessi et al.   |         |
| 4,539,996 | A |   | 9/1985  | Engel          |         |
| 4,541,734 | A |   | 9/1985  | Ishizaka       |         |
| 4,554,924 | A |   | 11/1985 | Engel          |         |

(Continued)

FOREIGN PATENT DOCUMENTS

EP 1748289 A2 1/2007
JP 61003019 1/1986

(Continued)

OTHER PUBLICATIONS

Akyldiz, I.F. et al.; "Wireless Multimedia Sensor Networks: A survey." IEEE Wireless Communications. Dec. 2007, p. 32-39.

(Continued)

*Primary Examiner* — Sean Dougherty
(74) *Attorney, Agent, or Firm* — McDermott Will & Emery LLP

(57) ABSTRACT

Systems and methods of monitoring the axillary temperature of a person are disclosed. A portion of a temperature probe is provided within the axilla of the person. The temperature probe includes a wiring portion and a body connection portion and a sensing portion between the wiring and body connection portions. The sensing portion comprises a temperature sensing element. The wiring portion is coupled to a monitoring device and comprises a conductor having a first end and a second end, the first end coupled to the temperature sensing element, and the second end connected to the monitoring device. At least a portion of the body connection portion is attached to a second body portion of the person, such that the sensing portion is retained within the axilla.

18 Claims, 17 Drawing Sheets

(56) References Cited

U.S. PATENT DOCUMENTS

| | | |
|---|---|---|
| 4,640,289 A | 2/1987 | Craighead |
| 4,686,998 A * | 8/1987 | Robbins .................. 600/549 |
| 4,708,146 A | 11/1987 | Lane |
| 4,715,382 A | 12/1987 | Strand |
| 4,765,340 A | 8/1988 | Sakai et al. |
| 4,771,713 A | 9/1988 | Kinzenbaw |
| 4,838,273 A | 6/1989 | Cartmell |
| 4,846,185 A | 7/1989 | Carim |
| 4,848,353 A | 7/1989 | Engel |
| 4,967,765 A | 11/1990 | Turner et al. |
| 5,012,810 A | 5/1991 | Strand et al. |
| 5,050,612 A * | 9/1991 | Matsumura .................. 600/483 |
| 5,094,545 A * | 3/1992 | Larsson ................ G01K 11/06 116/217 |
| 5,133,356 A | 7/1992 | Bryan et al. |
| 5,153,584 A | 10/1992 | Engira |
| 5,215,087 A | 6/1993 | Anderson et al. |
| 5,258,577 A | 11/1993 | Clements |
| 5,273,036 A | 12/1993 | Kronberg et al. |
| 5,285,577 A | 2/1994 | Carney et al. |
| 5,344,335 A | 9/1994 | Scholz et al. |
| 5,353,793 A * | 10/1994 | Bornn .................. 600/386 |
| 5,401,100 A * | 3/1995 | Thackston et al. ............ 374/208 |
| 5,511,553 A * | 4/1996 | Segalowitz .................. 600/508 |
| 5,544,661 A | 8/1996 | Davis et al. |
| 5,803,915 A * | 9/1998 | Kremenchugsky ...... A61B 5/01 374/29 |
| 5,980,467 A | 11/1999 | Henry |
| 6,030,342 A | 2/2000 | Amano et al. |
| 6,042,966 A | 3/2000 | Cheu |
| 6,090,050 A | 7/2000 | Constantinides |
| 6,222,456 B1 | 4/2001 | Tice |
| 6,270,252 B1 | 8/2001 | Siefert |
| 6,273,886 B1 | 8/2001 | Edwards et al. |
| 6,287,252 B1 | 9/2001 | Lugo |
| 6,324,426 B1 | 11/2001 | Thompson |
| 6,355,031 B1 | 3/2002 | Edwards et al. |
| 6,358,245 B1 | 3/2002 | Edwards et al. |
| 6,416,471 B1 | 7/2002 | Kumar et al. |
| 6,454,708 B1 | 9/2002 | Ferguson et al. |
| 6,468,261 B1 | 10/2002 | Small et al. |
| 6,472,612 B2 | 10/2002 | Fartash et al. |
| 6,472,614 B1 | 10/2002 | Dupont et al. |
| 6,494,829 B1 * | 12/2002 | New et al. .................. 600/300 |
| 6,517,497 B2 | 2/2003 | Rymut et al. |
| 6,636,754 B1 | 10/2003 | Baura et al. |
| 6,740,049 B2 | 5/2004 | Wallach |
| 6,740,059 B2 | 5/2004 | Flaherty |
| 6,950,688 B2 | 9/2005 | Axelgaard et al. |
| 6,963,772 B2 | 11/2005 | Bloom et al. |
| 6,980,112 B2 | 12/2005 | Nee |
| 7,052,472 B1 | 5/2006 | Miller et al. |
| 7,061,858 B1 | 6/2006 | Di Benedetto et al. |
| 7,198,600 B2 | 4/2007 | Tamaki et al. |
| 7,319,895 B2 * | 1/2008 | Klefstad-Sillonville A41D 13/1281 600/388 |
| 7,355,512 B1 | 4/2008 | Al-Ali |
| RE40,470 E | 8/2008 | Fitzpatrick et al. |
| 7,434,991 B2 | 10/2008 | Harr et al. |
| 7,447,526 B2 | 11/2008 | Kim et al. |
| 7,538,682 B2 | 5/2009 | Trost et al. |
| 7,542,437 B1 | 6/2009 | Redi et al. |
| 7,639,352 B2 | 12/2009 | Huber et al. |
| 7,639,652 B1 | 12/2009 | Amis et al. |
| 7,645,263 B2 | 1/2010 | Angel et al. |
| 7,668,588 B2 * | 2/2010 | Kovacs .................. 600/509 |
| 7,924,150 B2 | 4/2011 | Baldus et al. |
| 7,959,574 B2 | 6/2011 | Bardy |
| 7,962,188 B2 | 6/2011 | Kiani et al. |
| 8,007,436 B2 * | 8/2011 | Katayama .................. 600/301 |
| 8,200,320 B2 * | 6/2012 | Kovacs .................. 600/513 |
| 8,226,572 B2 | 7/2012 | Keith et al. |
| 8,228,188 B2 | 7/2012 | Key et al. |
| 8,231,542 B2 | 7/2012 | Keith et al. |
| 8,496,597 B2 | 7/2013 | James et al. |
| 8,506,480 B2 * | 8/2013 | Banet et al. .................. 600/301 |
| 8,721,562 B2 * | 5/2014 | Abreu .................. 600/549 |
| 2001/0047127 A1 * | 11/2001 | New et al. .................. 600/300 |
| 2002/0007676 A1 | 1/2002 | Ward et al. |
| 2002/0013538 A1 * | 1/2002 | Teller .................. 600/549 |
| 2002/0045836 A1 | 4/2002 | Alkawwas |
| 2002/0099277 A1 | 7/2002 | Harry et al. |
| 2002/0107436 A1 | 8/2002 | Barton et al. |
| 2002/0109621 A1 | 8/2002 | Khair et al. |
| 2002/0198519 A1 | 12/2002 | Qin et al. |
| 2003/0004403 A1 | 1/2003 | Drinan et al. |
| 2003/0040305 A1 | 2/2003 | Ng et al. |
| 2003/0069510 A1 | 4/2003 | Semler et al. |
| 2003/0191445 A1 | 10/2003 | Wallen et al. |
| 2003/0212319 A1 | 11/2003 | Magill |
| 2003/0212340 A1 | 11/2003 | Lussier et al. |
| 2003/0229809 A1 | 12/2003 | Wexler et al. |
| 2004/0015058 A1 | 1/2004 | Besson et al. |
| 2004/0030259 A1 | 2/2004 | Dae et al. |
| 2004/0062133 A1 | 4/2004 | Tsuji |
| 2004/0073132 A1 | 4/2004 | Maahs et al. |
| 2004/0116822 A1 * | 6/2004 | Lindsey .................. 600/549 |
| 2004/0165646 A1 | 8/2004 | Shidemantle et al. |
| 2004/0215098 A1 | 10/2004 | Barton et al. |
| 2004/0220538 A1 * | 11/2004 | Panopoulos ............ A61F 13/42 604/361 |
| 2004/0236188 A1 | 11/2004 | Hutchinson et al. |
| 2005/0085706 A1 | 4/2005 | Perrault et al. |
| 2005/0101843 A1 * | 5/2005 | Quinn et al. .................. 600/300 |
| 2005/0131288 A1 | 6/2005 | Turner et al. |
| 2005/0159653 A1 | 7/2005 | Lijima et al. |
| 2005/0195079 A1 | 9/2005 | Cohen |
| 2005/0228297 A1 | 10/2005 | Banet et al. |
| 2005/0228299 A1 | 10/2005 | Banet |
| 2005/0231350 A1 | 10/2005 | Littrell et al. |
| 2005/0245831 A1 | 11/2005 | Banet |
| 2005/0245839 A1 | 11/2005 | Stivoric et al. |
| 2005/0249263 A1 * | 11/2005 | Yerlikaya et al. .............. 374/209 |
| 2005/0251128 A1 | 11/2005 | Amoah |
| 2005/0280531 A1 | 12/2005 | Fadem et al. |
| 2006/0009697 A1 | 1/2006 | Banet et al. |
| 2006/0045165 A1 | 3/2006 | Chan et al. |
| 2006/0047987 A1 | 3/2006 | Prabhakaran et al. |
| 2006/0094971 A1 | 5/2006 | Drew |
| 2006/0098576 A1 | 5/2006 | Brownrigg et al. |
| 2006/0155183 A1 | 7/2006 | Kroecker et al. |
| 2006/0202816 A1 | 9/2006 | Crump et al. |
| 2006/0224349 A1 | 10/2006 | Butterfield |
| 2006/0276714 A1 | 12/2006 | Holt et al. |
| 2007/0032706 A1 | 2/2007 | Kamath et al. |
| 2007/0041424 A1 * | 2/2007 | Lev et al. .................. 374/163 |
| 2007/0099678 A1 | 5/2007 | Kim et al. |
| 2007/0116089 A1 | 5/2007 | Bisch et al. |
| 2007/0123756 A1 | 5/2007 | Kitajima et al. |
| 2007/0129622 A1 | 6/2007 | Bourget et al. |
| 2007/0135866 A1 | 6/2007 | Baker et al. |
| 2007/0142715 A1 | 6/2007 | Banet et al. |
| 2007/0185660 A1 | 8/2007 | Anderson |
| 2007/0191728 A1 | 8/2007 | Shennib |
| 2007/0208233 A1 * | 9/2007 | Kovacs .................. 600/300 |
| 2007/0219434 A1 * | 9/2007 | Abreu .................. 600/301 |
| 2007/0225614 A1 | 9/2007 | Naghavi et al. |
| 2007/0293781 A1 | 12/2007 | Sims et al. |
| 2008/0042866 A1 | 2/2008 | Morse et al. |
| 2008/0091090 A1 | 4/2008 | Guillory et al. |
| 2008/0097178 A1 | 4/2008 | Banet et al. |
| 2008/0097422 A1 | 4/2008 | Edwards et al. |
| 2008/0114220 A1 | 5/2008 | Banet et al. |
| 2008/0119707 A1 | 5/2008 | Stafford |
| 2008/0143512 A1 | 6/2008 | Wakisaka et al. |
| 2008/0183054 A1 | 7/2008 | Kroeger et al. |
| 2008/0200770 A1 | 8/2008 | Hubinette |
| 2008/0200774 A1 | 8/2008 | Luo |
| 2008/0208026 A1 | 8/2008 | Noujaim et al. |
| 2008/0214949 A1 | 9/2008 | Stivoric et al. |
| 2008/0221399 A1 | 9/2008 | Zhou et al. |
| 2008/0234600 A1 | 9/2008 | Marsh |
| 2008/0275327 A1 | 11/2008 | Faarbaek et al. |

(56) References Cited

U.S. PATENT DOCUMENTS

| | | | |
|---|---|---|---|
| 2008/0294065 A1* | 11/2008 | Waldhoff et al. | 600/549 |
| 2008/0305154 A1 | 12/2008 | Yanaki | |
| 2009/0018409 A1* | 1/2009 | Banet et al. | 600/301 |
| 2009/0054737 A1 | 2/2009 | Magar et al. | |
| 2009/0062670 A1 | 3/2009 | Sterling et al. | |
| 2009/0069642 A1 | 3/2009 | Gao et al. | |
| 2009/0076336 A1* | 3/2009 | Mazar | A61B 5/0402 600/300 |
| 2009/0076340 A1 | 3/2009 | Libbus et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076345 A1 | 3/2009 | Manicka et al. | |
| 2009/0076346 A1 | 3/2009 | James et al. | |
| 2009/0076350 A1 | 3/2009 | Bly et al. | |
| 2009/0076363 A1 | 3/2009 | Bly et al. | |
| 2009/0076364 A1 | 3/2009 | Libbus et al. | |
| 2009/0076405 A1 | 3/2009 | Amurthur et al. | |
| 2009/0076559 A1 | 3/2009 | Libbus et al. | |
| 2009/0105549 A1 | 4/2009 | Smith et al. | |
| 2009/0105605 A1* | 4/2009 | Abreu | 600/549 |
| 2009/0131759 A1 | 5/2009 | Sims et al. | |
| 2009/0131774 A1 | 5/2009 | Sweitzer et al. | |
| 2009/0182204 A1 | 7/2009 | Semler et al. | |
| 2009/0203974 A1 | 8/2009 | Hickle | |
| 2009/0209896 A1 | 8/2009 | Selevan | |
| 2009/0227877 A1 | 9/2009 | Tran | |
| 2009/0259139 A1* | 10/2009 | Stepien et al. | 600/549 |
| 2009/0270744 A1 | 10/2009 | Prstojevich et al. | |
| 2009/0271681 A1 | 10/2009 | Piret et al. | |
| 2009/0306536 A1 | 12/2009 | Ranganathan et al. | |
| 2010/0010319 A1 | 1/2010 | Tivig et al. | |
| 2010/0036212 A1 | 2/2010 | Rieth | |
| 2010/0056886 A1 | 3/2010 | Hurtubise et al. | |
| 2010/0056945 A1 | 3/2010 | Holmes | |
| 2010/0056946 A1 | 3/2010 | Holmes | |
| 2010/0056947 A1 | 3/2010 | Holmes | |
| 2010/0081949 A1 | 4/2010 | Derby, Jr. | |
| 2010/0100004 A1 | 4/2010 | van Someren | |
| 2010/0113894 A1 | 5/2010 | Padiy | |
| 2010/0121217 A1* | 5/2010 | Padiy | G01K 1/16 600/549 |
| 2010/0160745 A1 | 6/2010 | Hills et al. | |
| 2010/0222688 A1 | 9/2010 | Fischell et al. | |
| 2010/0234716 A1* | 9/2010 | Engel | A61B 5/02055 600/391 |
| 2010/0286607 A1 | 11/2010 | Saltzstein | |
| 2010/0292605 A1* | 11/2010 | Grassl | G01K 1/16 600/549 |
| 2010/0298656 A1 | 11/2010 | McCombie et al. | |
| 2010/0298895 A1 | 11/2010 | Ghaffari et al. | |
| 2010/0323634 A1 | 12/2010 | Kimura | |
| 2010/0324548 A1 | 12/2010 | Godara et al. | |
| 2011/0004076 A1 | 1/2011 | Janna et al. | |
| 2011/0060252 A1 | 3/2011 | Simonsen et al. | |
| 2011/0066062 A1 | 3/2011 | Banet et al. | |
| 2011/0077497 A1 | 3/2011 | Oster et al. | |
| 2011/0144470 A1 | 6/2011 | Mazar et al. | |
| 2011/0160601 A1 | 6/2011 | Wang et al. | |
| 2011/0176465 A1 | 7/2011 | Panta et al. | |
| 2011/0182213 A1 | 7/2011 | Forssell et al. | |
| 2011/0224557 A1 | 9/2011 | Banet et al. | |
| 2012/0029300 A1* | 2/2012 | Paquet | 600/300 |
| 2012/0029308 A1* | 2/2012 | Paquet | 600/301 |
| 2012/0029314 A1* | 2/2012 | Paquet et al. | 600/301 |
| 2012/0108920 A1 | 5/2012 | Bly et al. | |
| 2012/0165621 A1* | 6/2012 | Grayzel | A61B 5/00 600/301 |
| 2012/0238901 A1* | 9/2012 | Augustine | G01K 1/165 600/549 |
| 2012/0310070 A1 | 12/2012 | Kumar et al. | |

FOREIGN PATENT DOCUMENTS

| | | |
|---|---|---|
| JP | 2002-507131 | 3/2002 |
| JP | 2004-503266 | 2/2004 |
| JP | 2005-521453 | 7/2005 |
| JP | 2009-544065 | 12/2009 |
| KR | 20070097725 | 10/2007 |
| KR | 100949150 | 3/2010 |
| WO | WO90/12606 | 11/1990 |

OTHER PUBLICATIONS

Arisha, K. et al. "System-Level Power Optimization for wireless Multimedia Communication." Editors: Ramesh K. and Goodman, D.; Springer US; 2002, p. 21-40.

Cardei, M. et al.; "Improving Wireless Sensor Network Lifetime through Power Aware Organization"; Wireless Networks 11, 222-240. 2005.

Davidson, K. G. et al., "Measurement of tidal volume by using transthoracic impedance variations in rats," J. Appl. Physiol. 86:759-766, 1999.

Ernst. J.M. et al, "Impedance Penumography: noise as signal in impedance cardiography," Psychophysiology, 36 (1999) 333-338.

Freundlich J.J. et al., Electrical Impedance Pneumography for Simple Nonrestrictive Continuous Monitoring of Respiratory Rate, Rhythm and Tidal Volume for Surgical Patients, Chest, 65, p. 181-184, 1974.

Herman, T. et al.; "A Distributed TDMA Slot Assignment Algorithm for Wireless Sensor Networks"; S. Nikoletseas and J. Rolim (Eds.): Algosensors 2004, LNCS 3121, pp. 45-58, 2004, Springer-Verlag Berlin Heidelberg 2004.

Hohlt, B. et al. "Flexible Power Scheduling for Sensor Networks," IPSN'04, Apr. 26-27, 2004, Berkeley, California, USA. pp. 1-10.

Kelkar, S. P. et al., "Development of Movement artifact free breathing monitor," J. Instrum. Soc. India 38(1) 34-43, 2008.

Lee, W. L.; "Flexible-Schedule-Based TDMA Protocol for Fault-Tolerant and Energy-Efficient Wireless Sensor Networks," IEEE Transactions on Parallel and Distributed Systems, vol. 19, No. 6, Jun. 2008; p. 851-864.

Lee, W. L.; "Flexible-Schedule-Based TDMA Protocols for Supporting Fault-Tolerance, On-Demand TDMA Slot Transfer, and Peer-to-Peer Communication in Wireless Sensor Networks;" Thesis for the degree of Doctor in Philosophy, University of Western Australia, 2007, p. 1-213.

Loriga, G., et al., "Textile sensing interfaces for cardiopulmonary signs monitoring," Proceedings of the 2005 IEEE Engineering in Medicine and Biology 27th Annual Conference Shanghai, China, Sep. 1-4, 2005, p. 7349-7352.

Luo, S. et al., "The electrode system in Impedence-Based Ventilation Measurement," IEEE Transactions of biomedical Engineering, vol. 39, No. 11, Nov. 1992, p. 1130-1140.

Matthews, R., et al., "A Wearable Physiological Sensor Suite for Unobtrusive Monitoring of Physiological and Cognitive State," Proceedings of the 29th Annual International Conference of the IEEE EMBS Cite Internationale, Lyon, France, Aug. 23-26, 2007, pp. 1-6.

Pacela, A.F. "Impedance Pneumograph, a survey of instrumentation techniques," Med. & Biol. Engineering, vol. 4, p. 1-5, 1966.

Pantazis, N.A. et al.; "Energy efficiency in wireless sensor networks using sleep mode TDMA scheduling," Ad Hoc Networks 7 (2009) 322-343.

Paradiso, R. et al., "A wearable health care system based on knitted integrated sensors," IEEE transactions on Information Technology in biomedicine, vol. 9, No. 3, Sep. 2005, p. 337-344.

Park, et al., "Development of Flexible Self Adhesive Patch for Professional Heat Stress Monitoring Service," Proceedings of the 2005 IEEE Engineering in Medicine and Biology 27th Annual Conference Shanghai, China, Sep. 1-4, 2005, pp. 3789-3792.

Rashid, R. A. et al; "Development of Energy Aware TDMA-Based MAC Protocol for Wireless Sensor Network System," European Journal of Scientific, vol. 30 No. 4 (2009), pp. 571-578.

Shaw, G.A. et al., "Warfighter Physiological and Environmental Monitoring: A Study for the U.S. Army Research Institute in Environmental Medicine and the Soldier Systems Center," 2004, Lincoln Laboratory, MIT, pp. 1-141.

(56) References Cited

OTHER PUBLICATIONS

Zheng, W. W. et al. "Adaptive-frame-based Dynamic Slot Assignment Protocol for Tactical Data Link System," 2009 International Conference of Networks Security, Wireless Communications and Trusted Computing, IEEE, p. 709-714.
Final Office Action, dated Oct. 28, 2012 for U.S. Appl. No. 12/844,771.
Non-Final Office Action, dated Jun. 30, 2014 for U.S. Appl. No. 12/844,796.
Office Actions issued in U.S. Appl. No. 12/844,801, dated Aug. 14, 2014, and U.S. Appl. No. 12/844,794, dated Sep. 26, 2014.
Brown, B.H. et al., "Bipolar and Tetrapolar transfer impedence measurements from volume conductor," Electronics Letters, Wol. 35, No. 25, 2000, pp. 2060-2062.
Cooley, W.L. et al. "A new design for an impedence pneumograph," Journal of Applied Physiology, vol. 25, No. 4, 1968, pp. 429-432.
Grenvik, A. et al., "Impedence Pneumography," Chest, vol. 62, No. 4, Oct. 1972, pp. 439-443.
International Preliminary Report on Patentability in International Application No. PCT/US2011/030088, dated Oct. 27, 2012, 13 pages.
International Preliminary Report on Patentability in International Application No. PCT/US2011/045240, dated Jan. 29, 2013, 6 pages.
International Preliminary Report on Patentability in International Application No. PCT/US2011/045245, dated Jan. 29, 2013, 5 pages.
International Preliminary Report on Patentability in International Application No. PCT/US2011/045249, dated Jan. 29, 2013, 4 pages.
International Preliminary Report on Patentability in International Application No. PCT/US2011/045256, dated Jan. 29, 2013, 4 pages.
International Preliminary Report on Patentability in International Application No. PCT/US2011/045258, dated Jan. 29, 2013, 5 pages.
International Preliminary Report on Patentability in International Application No. PCT/US2011/045337, dated Jan. 9, 2013, 4 pages.
International Preliminary Report on Patentability in International Application No. PCT/US2011/045361, dated Jan. 29, 2013, 6 pages.
International Preliminary Report on Patentability in International Application No. PCT/US2011/045408, dated Jan. 29, 2013, 4 pages.
International Preliminary Report on Patentability in International Application No. PCT/US2011/045414, dated Jan. 29, 2013, 6 pages.
International Preliminary Report on Patentability in International Application No. PCT/US2011/045415, dated Jan. 29, 2013, 4 pages.
International Preliminary Report on Patentability in International Application No. PCT/US2011/045419, dated Jan. 29, 2013, 5 pages.
International Preliminary Report on Patentability in International Application No. PCT/US2011/045425, dated Jan. 29, 2013, 5 pages.
International Search Report and Written Opinion for International Application No. PCT/US2011/045408, dated Feb. 24, 2012, 6 pages.
International Search Report and Written Opinion in International Application No. PCT/US2011/045361, dated Apr. 6, 2012, 8 pages.
International Search Report and Written Opinion in International Application No. PCT/US2011/030088, dated Oct. 31, 2011, 7 pages.
International Search Report and Written Opinion in International Application No. PCT/US2011/045240, dated Mar. 15, 2012, 8 pages.
International Search Report and Written Opinion in International Application No. PCT/US2011/045245, dated Mar. 28, 2012, 7 pages.
International Search Report and Written Opinion in International Application No. PCT/US2011/045249, dated Mar. 12, 2012, 6 pages.
International Search Report and Written Opinion in International Application No. PCT/US2011/045256, dated Feb. 9, 2012, 12 pages.
International Search Report and Written Opinion in International Application No. PCT/US2011/045258, dated Apr. 6, 2012, 12 pages.
International Search Report and Written Opinion in International Application No. PCT/US2011/045337, dated Feb. 9, 2012, 7 pages.
International Search Report and Written Opinion in International Application No. PCT/US2011/045414, dated Feb. 24, 2012, 9 pages.
International Search Report and Written Opinion in International Application No. PCT/US2011/045415, dated Feb. 24, 2012, 7 pages.
International Search Report and Written Opinion in International Application No. PCT/US2011/045419, dated Apr. 6, 2012, 7 pages.
International Search Report and Written Opinion in International Application No. PCT/US2011/045425, dated Apr. 6, 2012, 7 pages.
Kessler, "TCP/IP and tcpdump Pocket reference Guide", Champlain College, 2006.
Murat, B., "Electrical Impedence Plethysmography," Wiley Encyclopedia of Biomedical Engineering, 2006, p. 1-10.
Poon, C.S. et al., "Evaluation of two noninvasive techniques for exercise ventilatory measurements," IEEE Engineering in Medicine and Biology Conference, 1988, pp. 0823-0824.
Sahakian, A.V. et al., "electrode Motion Artifacts in electrical Impedence Pneumography," IEEE Transactions in Biomedical Engineering, vol. BME-32, No. 6, Jun. 1985, pp. 448-451.
Zhihui Chen; Kohkhar, A. "Self organization and energy efficient TDMA MAC protocol by wake up for wireless sensor networks," Sensor and Ad Hoc Communications and Networks, 2004. IEEE SECON 2004. 2004 First Annual IEEE Communications Society Conference on, pp. 335-341. Oct. 2004.
Brown, B.H. et al., "Bipolar and Tetrapolar transfer impedence measurements from volume conductor," Electronics Letters, vol. 35, No. 25, 2000, pp. 2060-2062.
Cooley, W.L. et al., "A new design for an impedence pneumograph," Journal of Applied Physiology, vol. 25, No. 4, 1968, pp. 429-432.
Grenvik, A. et al., "Impedence Pneumography," Chest, vol. 62, No. 4, Oct. 1972, pp. 439-443.
Holt, T. et al., "Monitoring and recording of physiological data of the manned space flight program," Supplement to IEEE Transactions on Aerospace, Jun. 1965, p. 341-344.
Miller, Matthew J., et al., "On-Demand TDMA Scheduling for Energy Conservation in Sensor Networks," Technical Report, Jun. 2004.
Murat, B., "Electrical Impedence Plethysmography," Wiley Encyclopedia of Biomedical Engineering, 2006, p. 1-10.
NPL_VitalSense_2006, p. 1-2.
Poon, C. S. et al., "Evaluation of two noninvasive techniques for exercise ventilatory measurements," IEEE Engineering in Medicine and Biology conference, 1988, pp. 0823-0824.
Shakian, A. V. et al., "Electrode Motion Artifacts in Electrical Impedence Pneumography," IEEE Transactions in Biomedical Engineering, vol. BME-32, No. 6, Jun. 1985, pp. 448-451.

\* cited by examiner

TEMPERATURE PROBE SUITABLE FOR AXILLARY READING

CROSS-REFERENCES TO RELATED APPLICATIONS

The following applications disclose certain common subject matter with the present application: A Vital-Signs Monitor with Encapsulation Arrangement, U.S. patent application Ser. No. 12/844,766; A Vital-Signs Monitor with Spaced Electrodes, U.S. patent application Ser. No. 12/844,769; A Vital-Signs Patch Having a Strain Relief, U.S. patent application Ser. No. 12/844,774; System and Method for Monitoring Body Temperature of a Person, U.S. patent application Ser. No. 12/844,771; A System and Method for Storing and Forwarding Data from a Vital-Signs Monitor, U.S. patent application Ser. No. 12/844,780; System and Method for Saving Battery Power in a Vital Signs Monitor, U.S. patent application Ser. No. 12/844,789; A System and Method for Conserving Battery Power in a Patient Monitoring System, U.S. patent application Ser. No. 12/844,796; A System and Method for Saving Battery Power in a Patient Monitoring System, U.S. patent application Ser. No. 12/844,801; A System And Method for Tracking Vital-Signs Monitor Patches, U.S. patent application Ser. No. 12/844,788; A System And Method for Reducing False Alarms Associated with Vital-Signs Monitoring, U.S. patent application Ser. No. 12/844,794; A System And Method for Location Tracking of Patients in a Vital-Signs Monitoring System, U.S. patent application Ser. No. 12/844,781; A System And Method for Reducing False Alarms Based on Motion and Location Sensing, U.S. patent application Ser. No. 12/844,765; all of the listed applications filed on Jul. 27, 2010.

FIELD

The present disclosure generally relates to systems and methods of physiological monitoring, and, in particular, relates to a temperature probe suitable for axillary reading.

DESCRIPTION OF THE RELATED ART

Some of the most basic indicators of a person's health are those physiological measurements that reflect basic body functions and are commonly referred to as a person's "vital signs." The four measurements commonly considered to be vital signs are body temperature, pulse rate, blood pressure, and respiratory rate. Some clinicians consider oxygen saturation ($S_{O2}$) to be a "fifth vital sign" particularly for pediatric or geriatric cases. Some or all of these measurements may be performed routinely upon a patient when they arrive at a healthcare facility, whether it is a routine visit to their doctor or arrival at an Emergency Room (ER).

Vital signs are frequently taken by a nurse using basic tools including a thermometer to measure body temperature, a sphygmomanometer to measure blood pressure, and a watch to count the number of breaths or the number of heart beats in a defined period of time which is then converted to a "per minute" rate. If a patient's pulse is weak, it may not be possible to detect a pulse by hand and the nurse may use a stethoscope to amplify the sound of the patient's heart beat so that she can count the beats. Oxygen saturation of the blood is most easily measured with a pulse oximeter.

When a patient is admitted to a hospital, it is common for vital signs to be measured and recorded at regular intervals during the patient's stay to monitor their condition. A typical interval is 4 hours, which leads to the undesirable requirement for a nurse to awaken a patient in the middle of the night to take vital sign measurements.

When a patient is admitted to an ER, it is common for a nurse to do a "triage" assessment of the patient's condition that will determine how quickly the patient receives treatment. During busy times in an ER, a patient who does not appear to have a life-threatening injury may wait for hours until more-serious cases have been treated. While the patient may be reassessed at intervals while awaiting treatment, the patient may not be under observation between these reassessments.

Measuring certain vital signs is normally intrusive at best and difficult to do on a continuous basis. Measurement of body temperature, for example, is commonly done by placing an oral thermometer under the tongue or placing an infrared thermometer in the ear canal such that the tympanic membrane, which shared blood circulation with the brain, is in the sensor's field of view. Another method of taking a body temperature is by placing a thermometer under the arm, referred to as an "axillary" measurement as axilla is the Latin word for armpit. Skin temperature can be measured using a stick-on strip that may contain panels that change color to indicate the temperature of the skin below the strip.

Measurement of respiration is easy for a nurse to do, but relatively complicated for equipment to achieve. A method of automatically measuring respiration is to encircle the upper torso with a flexible band that can detect the physical expansion of the rib cage when a patient inhales. An alternate technique is to measure a high-frequency electrical impedance between two electrodes placed on the torso and detect the change in impedance created when the lungs fill with air. The electrodes are typically placed on opposite sides of one or both lungs, resulting in placement on the front and back or on the left and right sides of the torso, commonly done with adhesive electrodes connected by wires or by using a torso band with multiple electrodes in the strap.

Measurement of pulse is also relatively easy for a nurse to do and intrusive for equipment to achieve. A common automatic method of measuring a pulse is to use an electrocardiograph (ECG or EKG) to detect the electrical activity of the heart. An EKG machine may use 12 electrodes placed at defined points on the body to detect various signals associated with the heart function. Another common piece of equipment is simply called a "heart rate monitor." Widely sold for use in exercise and training, heart rate monitors commonly consist of a torso band, in which are embedded two electrodes held against the skin and a small electronics package. Such heart rate monitors can communicate wirelessly to other equipment such as a small device that is worn like a wristwatch and that can transfer data wirelessly to a PC.

Nurses are expected to provide complete care to an assigned number of patients. The workload of a typical nurse is increasing, driven by a combination of a continuing shortage of nurses, an increase in the number of formal procedures that must be followed, and an expectation of increased documentation. Replacing the manual measurement and logging of vital signs with a system that measures and records vital signs would enable a nurse to spend more time on other activities and avoid the potential for error that is inherent in any manual procedure.

SUMMARY

For some or all of the reasons listed above, there is a need to be able to continuously monitor patients in different settings. In addition, it is desirable for this monitoring to be done with limited interference with a patient's mobility or interfering with their other activities.

Embodiments of the patient monitoring system disclosed herein measure certain vital signs of a patient, which include respiratory rate, pulse rate, blood pressure, body temperature, and, in some cases, oxygen saturation ($S_{O2}$), on a regular basis and compare these measurements to defined limits.

In one aspect of the present disclosure, a temperature probe for axillary temperature reading of a person is provided. The temperature probe can comprise a sensing portion configured for placement within the axilla of a person and having a first end and a second end. The sending portion can comprise a temperature sensing element configured to provide a signal responsive to a change in body temperature of the person. The temperature probe can further comprise a wiring portion having one end connected to the first end of the sensing portion and comprising an electrical conductor, the electrical conductor having a first end configured for coupling to a monitoring device, and a second end connected to the temperature sensing element, the electrical connector configured to carry the signal from the temperature sensing element to the monitoring device. The temperature probe can further comprise a body connection portion having one end connected to the second end of the sensing portion and configured to be attached to another body portion of the person.

In one aspect of the present disclosure, a system for body temperature monitoring of a person through axillary measurement is provided. The system can comprise a temperature probe comprising a cable and a temperature sensing element, configured such that the temperature sensing element is to be retained in the axilla of the person at least during body temperature monitoring. The system can further comprise a monitoring device worn by the person and connected to the cable, the monitoring device receiving signals from the temperature sensing element. The monitoring device can include a wireless communication system to wirelessly transmit readings representative of sensed body temperatures of the person as determined by the monitoring device based on the signals received from the temperature sensing element.

In one aspect of the present disclosure, a method of monitoring the axillary temperature of a person is disclosed. The method can comprise providing a portion of a temperature probe within the axilla of the person, the temperature probe comprising a wiring portion and a body connection portion and a sensing portion between the wiring and body connection portions, the sensing portion comprising a temperature sensing element, the wiring portion coupled to a monitoring device and comprising a conductor having a first end and a second end, the first end coupled to the temperature sensing element, and the second end connected to the monitoring device. The method can further comprise attaching at least a portion of the body connection portion to a second body portion of the person, such that the sensing portion is retained within the axilla.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
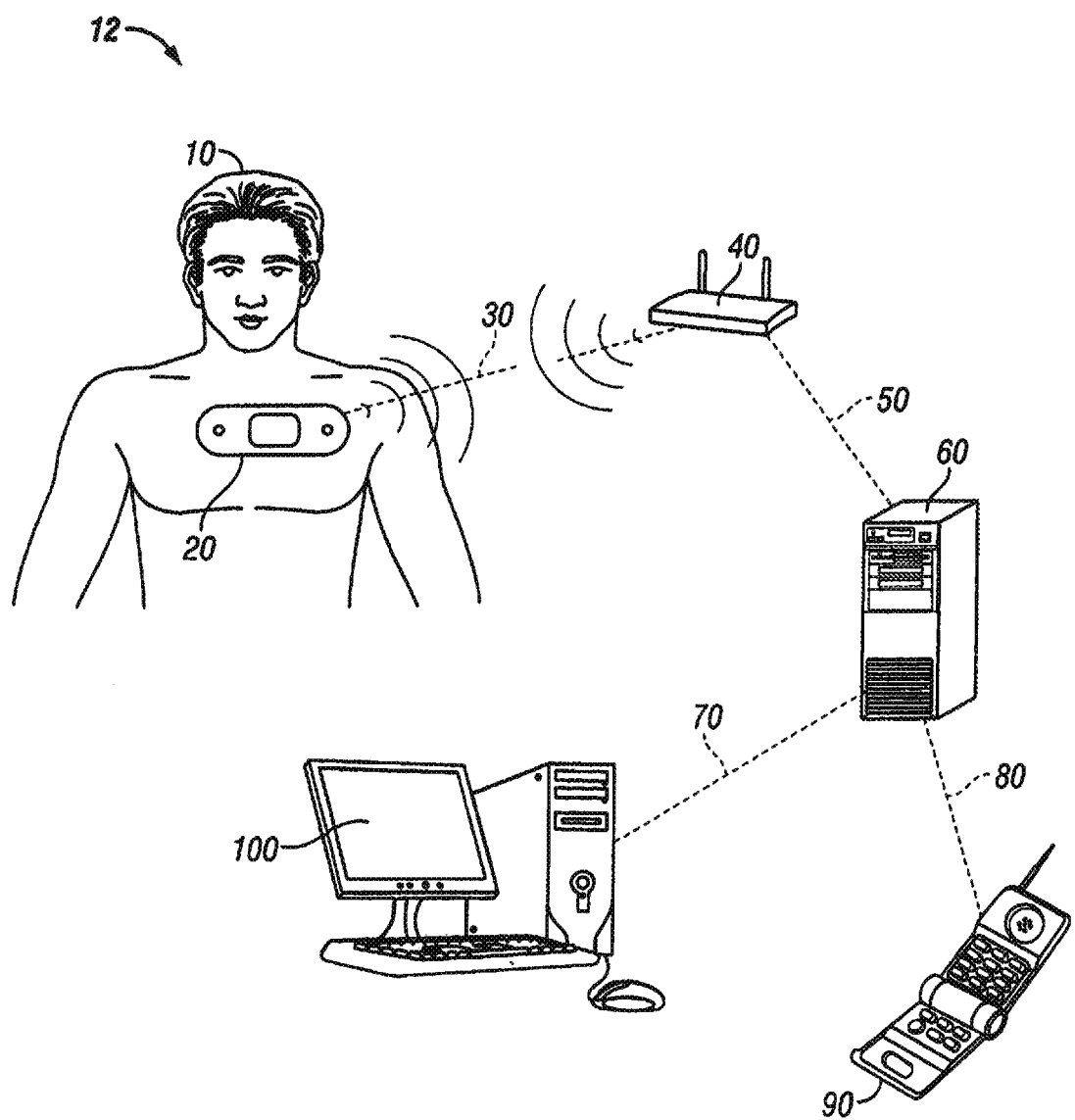
FIG. 1 is a diagram illustrating an exemplary embodiment of a patient monitoring system according to certain aspects of the present disclosure.

Periodic monitoring of patients in a hospital is desirable at least to ensure that patients do not suffer an un-noticed sudden deterioration in their condition or a secondary injury during their stay in the hospital. It is impractical to provide continuous monitoring by a clinician and cumbersome to connect sensors to a patient, which are then connected to a fixed monitoring instrument by wires. Furthermore, systems that sound an alarm when the measured value exceeds a threshold value may sound alarms so often and in situations that are not truly serious that such alarms are ignored by clinicians.

Measuring vital signs is difficult to do on a continuous basis. Accurate measurement of cardiac pulse, for example, can be done using an electrocardiograph (ECG or EKG) to detect the electrical activity of the heart. An EKG machine may use up to 12 electrodes placed at various points on the body to detect various signals associated with the cardiac function. Another common piece of equipment is termed a "heart rate monitor." Widely sold for use in exercise and physical training, heart rate monitors may comprise a torso band in which are embedded two electrodes held against the skin and a small electronics package. Such heart rate monitors can communicate wirelessly to other equipment such as a small device that is worn like a wristwatch and that can transfer data wirelessly to a personal computer (PC).

Monitoring of patients that is referred to as "continuous" is frequently periodic, in that measurements are taken at intervals. In many cases, the process to make a single measurement takes a certain amount of time, such that even back-to-back measurements produce values at an interval equal to the time that it takes to make the measurement. For the purpose of vital sign measurement, a sequence of repeated measurements can be considered to be "continuous" when the vital sign is not likely to change an amount that is of clinical significance within the interval between measurements. For example, a measurement of blood pressure every 10 minutes may be considered "continuous" if it is considered unlikely that a patient's blood pressure can change by a clinically significant amount within 10 minutes. The interval appropriate for measurements to be considered continuous may depend on a variety of factors including the type of injury or treatment and the patient's medical history. Compared to intervals of 4-8 hours for manual vital sign measurement in a hospital, measurement intervals of 30 minutes to several hours may still be considered "continuous."

Certain exemplary embodiments of the present disclosure include a system that comprises a vital-signs monitor patch that is attached to the patient, and a bridge that communicates with monitor patches and links them to a central server that processes the data, where the server can send data and alarms to a hospital system according to algorithms and protocols defined by the hospital.

The construction of the vital-signs monitor patch is described according to certain aspects of the present disclosure. As the patch may be worn continuously for a period of time that may be several days, as is described in the following disclosure, it is desirable to encapsulate the components of the patch such that the patient can bathe or shower and engage in their normal activities without degradation of the patch function. An exemplary configuration of the construction of the patch to provide a hermetically sealed enclosure about the electronics is disclosed.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

FIG. 1 discloses a vital sign monitoring system according to certain embodiments of the present disclosure. The vital sign monitoring system 12 includes vital-signs monitor patch 20, bridge 40, and surveillance server 60 that can send messages or interact with peripheral devices exemplified by mobile device 90 and workstation 100.

Monitor patch 20 resembles a large adhesive bandage and is applied to a patient 10 when in use. It is preferable to apply the monitor patch 20 to the upper chest of the patient 10 although other locations may be appropriate in some circumstances. Monitor patch 20 incorporates one or more electrodes (not shown) that are in contact with the skin of patient 10 to measure vital signs such as cardiac pulse rate and respiration rate. Monitor patch 20 also may include other sensors such as an accelerometer, temperature sensor, or oxygen saturation sensor to measure other characteristics associated with the patient. These other sensors may be internal to the monitor patch 20 or external sensors that are operably connected to the monitor patch 20 via a cable or wireless connection. Monitor patch 20 also includes a wireless transmitter that can both transmit and receive signals. This transmitter is preferably a short-range, low-power radio frequency (RF) device operating in one of the unlicensed radio bands. One band in the United States (US) is, for example, centered at 915 MHz and designated for industrial, scientific and medical (ISM) purposes. An example of an equivalent band in the European Union (EU) is centered at 868 MHz. Other frequencies of operation may be possible dependent upon the International Telecommunication Union (ITU), local regulations and interference from other wireless devices.

Surveillance server 60 may be a standard or virtualized computer server connected to the hospital communication network and preferably located in the hospital data center or computer room, although other locations may be employed. The server 60 stores and processes signals related to the operation of the patient monitoring system 12 disclosed herein including the association of individual monitor patches 20 with patients 10 and measurement signals received from multiple monitor patches 20. Hence, although only a single patient 10 and monitor patch 20 are depicted in FIG. 1, the server 60 is able to monitor the monitor patches 20 for multiple patients 10.

Bridge 40 is a device that connects, or "bridges", between monitor patch 20 and server 60. Bridge 40 communicates with monitor patch 20 over communication link 30 operating, in these exemplary embodiments, at approximately 915 MHz and at a power level that enables communication link 30 to function up to a distance of approximately 10 meters. It is preferable to place a bridge 40 in each room and at regular intervals along hallways of the healthcare facility where it is desired to provide the ability to communicate with monitor patches 20. Bridge 40 also is able to communicate with server 60 over network link 50 using any of a variety of computer communication systems including hardwired and wireless Ethernet using protocols such as 802.11a/b/g or 802.3af. As the communication protocols of communication link 30 and network link 50 may be very different, bridge 40 provides data buffering and protocol conversion to enable bidirectional signal transmission between monitor patch 20 and server 60.

While the embodiments illustrated by FIG. 1 employ a bridge 20 to provide communication link between the monitor patch 20 and the server 60, in certain alternative embodiments, the monitor patch 20 may engage in direct wireless communication with the server 60. In such alternative embodiments, the server 60 itself or a wireless modem connected to the server 60 may include a wireless communication system to receive data from the monitor patch 20.

In use, a monitor patch 20 is applied to a patient 10 by a clinician when it is desirable to continuously monitor basic vital signs of patient 10 while patient 10 is, in this embodiment, in a hospital. Monitor patch 20 is intended to remain attached to patient 10 for an extended period of time, for example, up to 5 days in certain embodiments, limited by the battery life of monitor patch 20. In some embodiments, monitor patch 20 is disposable when removed from patient 10.

Server 60 executes analytical protocols on the measurement data that it receives from monitor patch 20 and provides this information to clinicians through external workstations 100, preferably personal computers (PCs), laptops, or smart phones, over the hospital network 70. Server 60 may also send messages to mobile devices 90, such as cell phones or pagers, over a mobile device link 80 if a measurement signal exceeds specified parameters. Mobile device link 80 may include the hospital network 70 and internal or external wireless communication systems that are capable of sending messages that can be received by mobile devices 90.

Figure 2A:
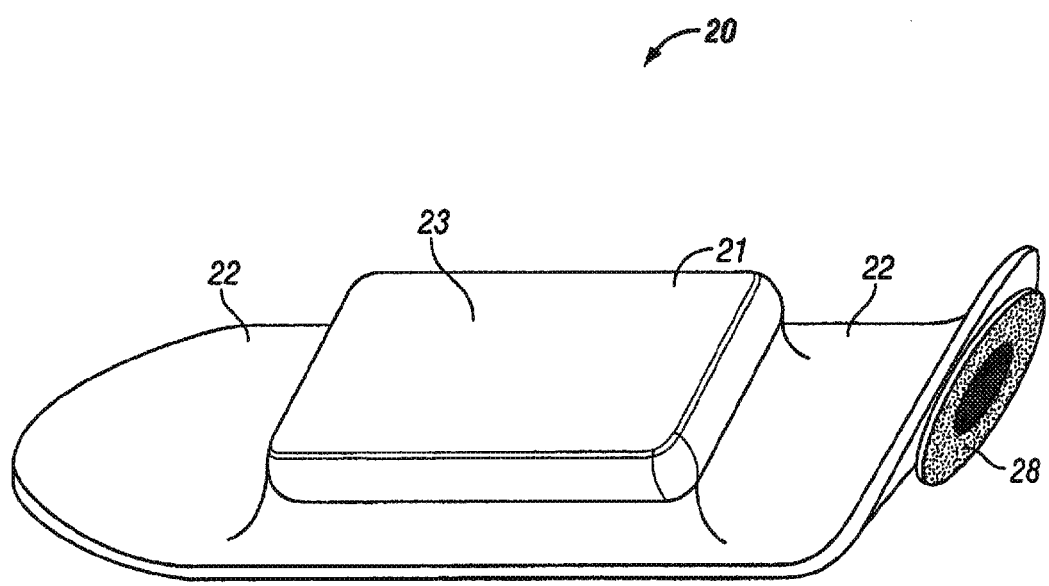
FIG. 2A is a perspective view of the vitals sign monitor patch shown in FIG. 1 according to certain aspects of the present disclosure.

FIG. 2A is a perspective view of the vital-signs monitor patch 20 shown in FIG. 1 according to certain aspects of the present disclosure. In the illustrated embodiment, the monitor patch 20 includes component carrier 23 comprising a central segment 21 and side segments 22 on opposing sides of the central segment 21. In certain embodiments, the central segment 21 is substantially rigid and includes a circuit assembly (24, FIG. 2B) having electronic components and battery mounted to a rigid printed circuit board (PCB). The side segments 22 are flexible and include a flexible conductive circuit (26, FIG. 2B) that connect the circuit assembly 24 to electrodes 28 disposed at each end of the monitor patch 20, with side segment 22 on the right shown as being bent upwards for purposes of illustration to make one of the electrodes 28 visible in this view.

Figure 2B:
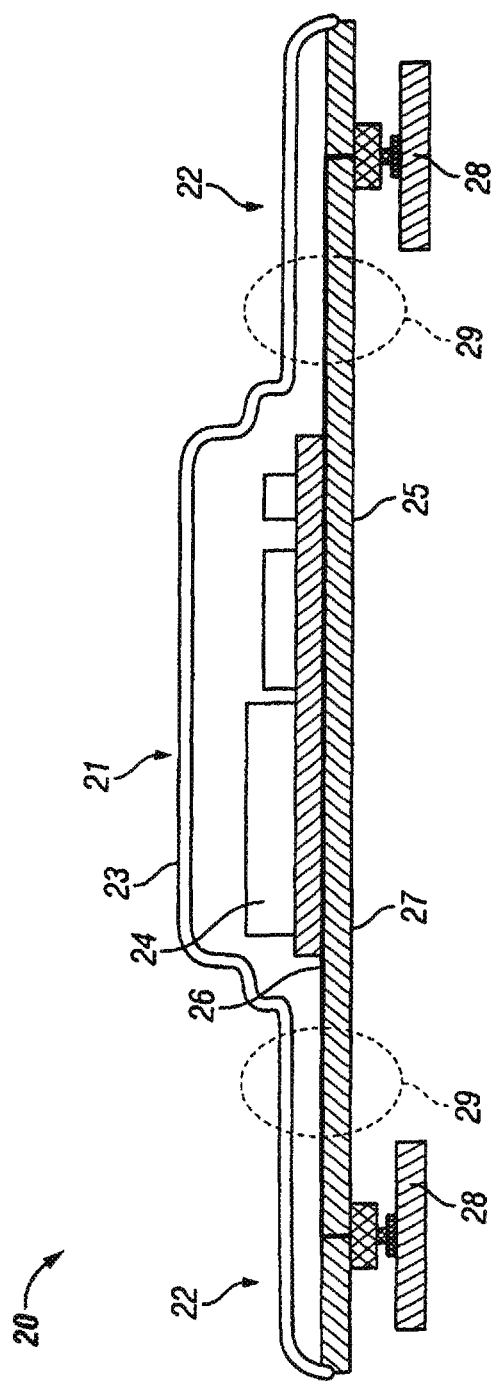
FIG. 2B is a cross-sectional view of the vital signs patch shown in FIGS. 1 and 2A according to certain aspects of the present disclosure.

FIG. 2B is a cross-sectional view of the vital-signs patch 20 shown in FIGS. 1 and 2A according to certain aspects of the present disclosure. The circuit assembly 24 and flexible conductive circuit 26 described above can be seen herein. The flexible conductive circuit 26 operably connects the circuit assembly 24 to the electrodes 28. Top and bottom layers 23 and 27 form a housing 25 that encapsulate circuit assembly 28 to provide a water and particulate barrier as well as mechanical protection. There are sealing areas on layers 23 and 27 that encircles circuit assembly 28 and is visible in the cross-section view of FIG. 2B as areas 29. Layers 23 and 27 are sealed to each other in this area to form a substantially hermetic seal. Within the context of certain aspects of the present disclosure, the term 'hermetic' implies that the rate of transmission of moisture through the seal is substantially the same as through the material of the layers that are sealed to each other, and further implies that the size of particulates that can pass through the seal are below the size that can have a significant effect on circuit assembly 24. Flexible conductive circuit 26 passes through portions of sealing areas 29 and the seal between layers 23 and 27 is maintained by sealing of layers 23 and 27 to flexible circuit assembly 28. The layers 23 and 27 are thin and flexible, as is the flexible conductive circuit 26, allowing the side segment 22 of the monitor patch 20 between the electrodes 28 and the circuit assembly 24 to bend as shown in FIG. 2A.

Figure 2C:
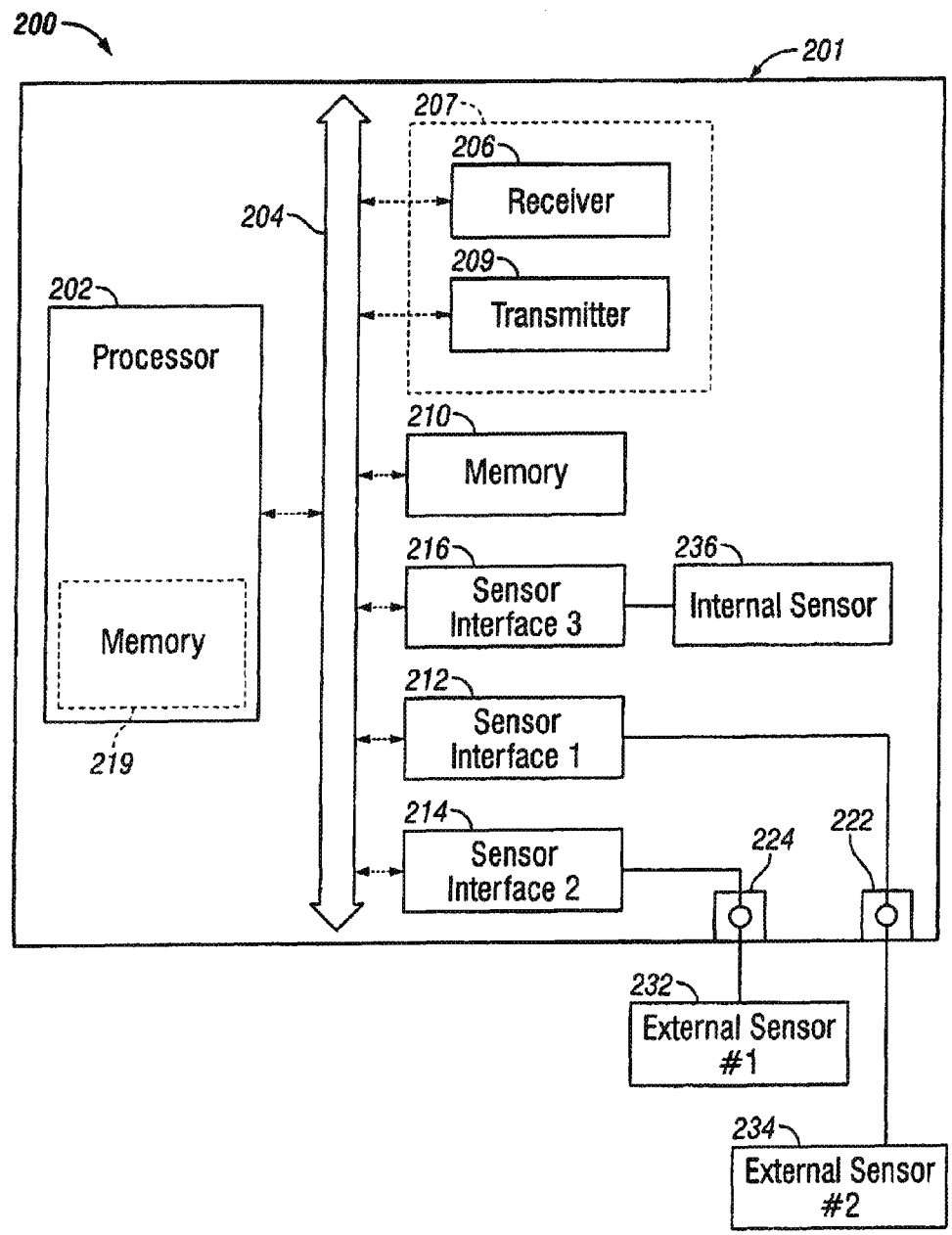
FIG. 2C is a functional block diagram illustrating exemplary electronic and sensor components of the monitor patch of FIG. 1 according to certain aspects of the present disclosure.

FIG. 2C is a functional block diagram 200 illustrating exemplary electronic and sensor components of the monitor patch 20 of FIG. 1 according to certain aspects of the present disclosure. The block diagram 200 shows a processing and sensor interface module 201 and external sensors 232, 234 connected to the module 201. In the illustrated example, the module 201 includes a processor 202, a wireless transceiver 207 having a receiver 206 and a transmitter 209, a memory 210, a first sensor interface 212, a second sensor interface 214, a third sensor interface 216, and an internal sensor 236 connected to the third sensor interface 216. The first and second sensor interfaces 212 and 214 are connected to the first and second external sensors 232, 234 via first and second connection ports 222, 224, respectively. In certain embodiments, some or all of the aforementioned components of the module 201 and other components are mounted on a PCB.

Each of the sensor interfaces 212, 214, 216 can include one or more electronic components that are configured to generate an excitation signal or provide DC power for the sensor that the interface is connected to and/or to condition and digitize a sensor signal from the sensor. For example, the sensor interface can include a signal generator for generating an excitation signal or a voltage regulator for providing power to the sensor. The sensor interface can further include an amplifier for amplifying a sensor signal from the sensor and an analog-to-digital converter for digitizing the amplified sensor signal. The sensor interface can further include a filter (e.g., a low-pass or bandpass filter) for filtering out spurious noises (e.g., a 60 Hz noise pickup).

The processor 202 is configured to send and receive data (e.g., digitized signal or control data) to and from the sensor interfaces 212, 214, 216 via a bus 204, which can be one or more wire traces on the PCB. Although a bus communication topology is used in this embodiment, some or all communication between discrete components can also be implemented as direct links without departing from the scope of the present disclosure. For example, the processor 202 may send data representative of an excitation signal to the sensor excitation signal generator inside the sensor interface and receive data representative of the sensor signal from the sensor interface, over either a bus or direct data links between processor 202 and each of sensor interface 212, 214, and 216.

The processor 202 is also capable of communication with the receiver 206 and the transmitter 209 of the wireless transceiver 207 via the bus 204. For example, the processor 202 using the transmitter and receiver 209, 206 can transmit and receive data to and from the bridge 40. In certain embodiments, the transmitter 209 includes one or more of a RF signal generator (e.g., an oscillator), a modulator (a mixer), and a transmitting antenna; and the receiver 206 includes a demodulator (a mixer) and a receiving antenna which may or may not be the same as the transmitting antenna. In some embodiments, the transmitter 209 may include a digital-to-analog converter configured to receive data from the processor 202 and to generate a base signal; and/or the receiver 206 may include an analog-to-digital converter configured to digitize a demodulated base signal and output a stream of digitized data to the processor 202.

The processor 202 may include a general-purpose processor or a specific-purpose processor for executing instructions and may further include a memory 219, such as a volatile or non-volatile memory, for storing data and/or instructions for software programs. The instructions, which may be stored in a memory 219 and/or 210, may be executed by the processor 202 to control and manage the wireless transceiver 207, the sensor interfaces 212, 214, 216, as well as provide other communication and processing functions.

The processor 202 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information, such as program instructions, data representative of sensor readings, preset alarm conditions, threshold limits, may be stored in a computer or processor readable medium such as a memory internal to the processor 202 (e.g., the memory 219) or a memory external to the processor 202 (e.g., the memory 210), such as a Random Access Memory (RAM), a flash memory, a Read Only Memory (ROM), a Programmable Read-Only Memory (PROM), an Erasable PROM (EPROM), registers, a hard disk, a removable disk, or any other suitable storage device.

In certain embodiments, the internal sensor 236 can be one or more sensors configured to measure certain properties of the processing and sensor interface module 201, such as a board temperature sensor thermally coupled to a PCB. In other embodiments, the internal sensor 236 can be one or more sensors configured to measure certain properties of the patient 10, such as a motion sensor (e.g., an accelerometer) for measuring the patient's motion or position with respect to gravity.

The external sensors 232, 234 can include sensors and sensing arrangements that are configured to produce a signal representative of one or more vital signs of the patient to which the monitor patch 20 is attached. For example, the first external sensor 232 can be a set of sensing electrodes that are affixed to an exterior surface of the monitor patch 20 and configured to be in contact with the patient for measuring the patient's respiratory rate, and the second external sensor 234 can include a temperature sensing element (e.g., a thermocouple or a thermistor or resistive thermal device (RTD)) affixed, either directly or via an interposing layer, to skin of the patient 10 for measuring the patient's body temperature. In other embodiments, one or more of the external sensors 232, 234 or one or more additional external sensors can measure other vital signs of the patient, such as blood pressure, pulse rate, or oxygen saturation.

Figure 3A:
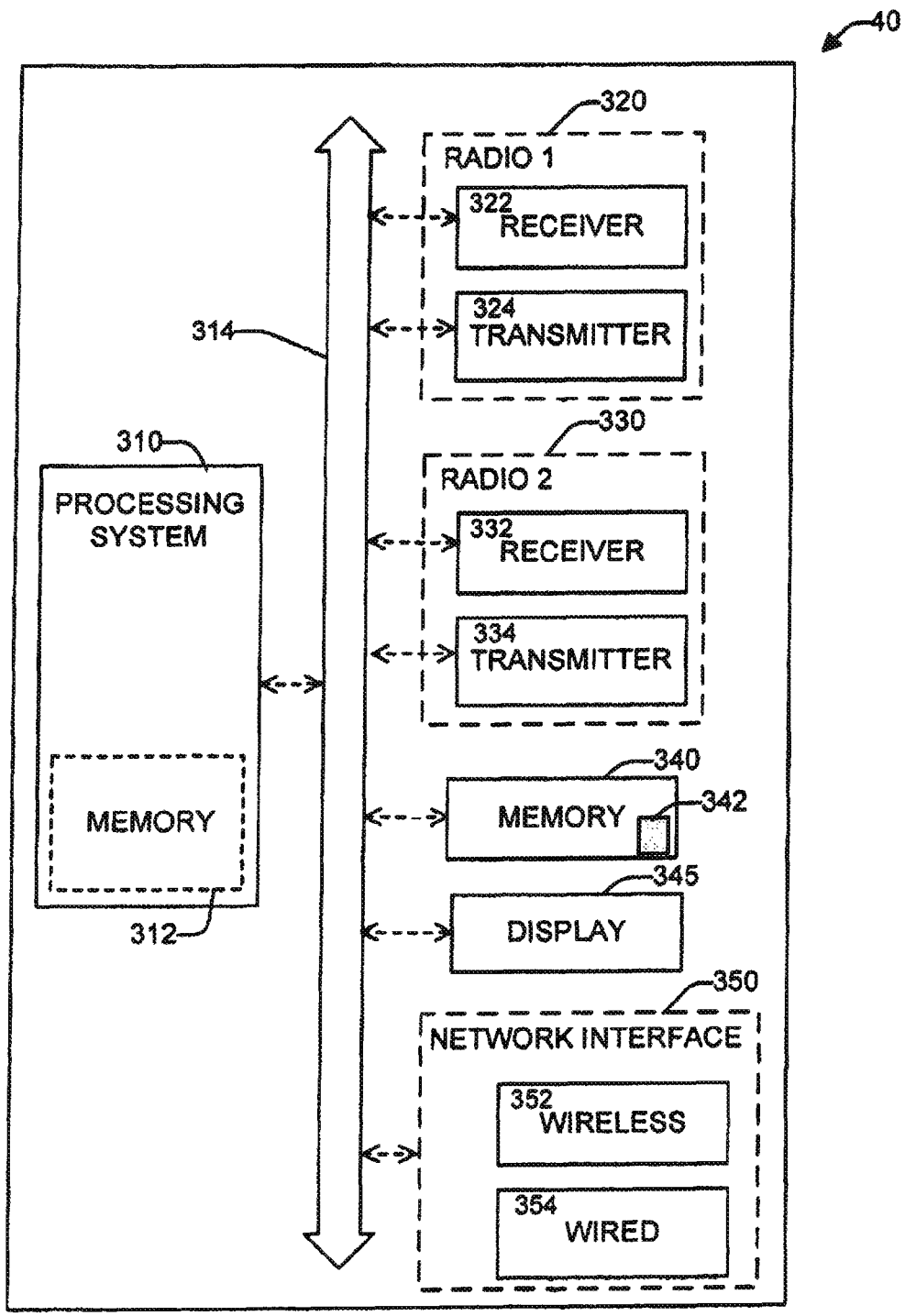
FIG. 3A is a functional schematic diagram of an embodiment of the bridge according to certain aspects of the present disclosure.

FIG. 3A is a functional block diagram illustrating exemplary electronic components of bridge 40 of FIG. 1 according to one aspect of the subject disclosure. Bridge 40 includes a processor 310, radio 320 having a receiver 322 and a transmitter 324, radio 330 having a receiver 332 and a transmitter 334, memory 340, display 345, and network interface 350 having a wireless interface 352 and a wired interface 354. In some embodiments, some or all of the aforementioned components of module 300 may be integrated into single devices or mounted on PCBs.

Processor 310 is configured to send data to and receive data from receiver 322 and transmitter 324 of radio 320, receiver 332 and transmitter 334 of radio 330 and wireless interface 352 and wired interface 354 of network interface 350 via bus 314. In certain embodiments, transmitters 324 and 334 may include a radio frequency signal generator (oscillator), a modulator, and a transmitting antenna, and the receivers 322 and 332 may include a demodulator and antenna which may or may not be the same as the transmitting antenna of the radio. In some embodiments, transmitters 324 and 334 may include a digital-to-analog converter configured to convert data received from processor 310 and to generate a base signal, while receivers 322 and 332 may include analog-to-digital converters configured to convert a demodulated base signal and sent a digitized data stream to processor 310.

Processor 310 may include a general-purpose processor or a specific-purpose processor for executing instructions and may further include a memory 312, such as a volatile or non-volatile memory, for storing data and/or instructions for software programs. The instructions, which may be stored in memories 312 or 340, may be executed by the processor 310 to control and manage the transceivers 320, 330, and 350 as well as provide other communication and processing functions.

Processor 310 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information such as data representative of sensor readings may be stored in memory 312 internal to processor 310 or in memory 340 external to processor 310 which may be a Random Access Memory (RAM), flash memory, Read Only Memory (ROM), Programmable Read Only Memory (PROM), Erasable Programmable Read Only Memory (EPROM), registers, a hard disk, a removable disk, a Solid State Memory (SSD), or any other suitable storage device.

Memory 312 or 340 can also store a list or a database of established communication links and their corresponding characteristics (e.g., signal levels) between the bridge 40 and its related monitor patches 20. In the illustrated example of FIG. 3A, the memory 340 external to the processor 310 includes such a database 342; alternatively, the memory 312 internal to the processor 310 may include such a database.

Figure 3B:
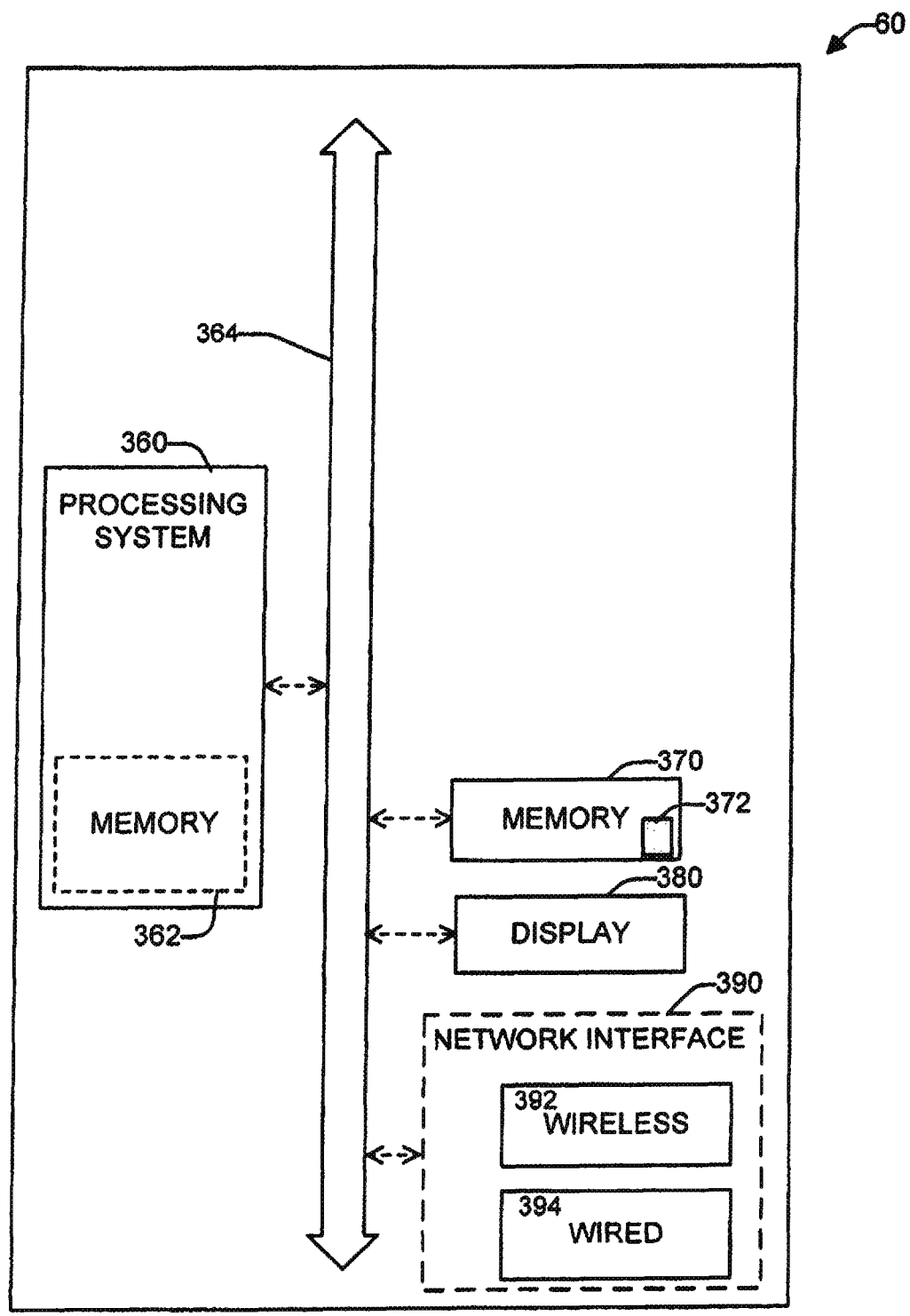
FIG. 3B is a functional schematic diagram of an embodiment of the surveillance server according to certain aspects of the present disclosure.

FIG. 3B is a functional block diagram illustrating exemplary electronic components of server 60 of FIG. 1 according to one aspect of the subject disclosure. Server 60 includes a processor 360, memory 370, display 380, and network interface 390 having a wireless interface 392 and a wired interface 394. Processor 360 may include a general-purpose processor or a specific-purpose processor for executing instructions and may further include a memory 362, such as a volatile or non-volatile memory, for storing data and/or instructions for software programs. The instructions, which may be stored in memories 362 or 370, may be executed by the processor 360 to control and manage the wireless and wired network interfaces 392, 394 as well as provide other communication and processing functions.

Processor 360 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information such as data representative of sensor readings may be stored in memory 362 internal to processor 360 or in memory 370 external to processor 360 which may be a Random Access Memory (RAM), flash memory, Read Only Memory (ROM), Programmable Read Only Memory (PROM), Erasable Programmable Read Only Memory (EPROM), registers, a hard disk, a removable disk, a Solid State Memory (SSD), or any other suitable storage device.

Memory 362 or 370 can also store a database of communication links and their corresponding characteristics (e.g., signal levels) between monitor patches 20 and bridges 40. In the illustrated example of FIG. 3B, the memory 370 external to the processor 360 includes such a database 372; alternatively, the memory 362 internal to the processor 360 may include such a database.

Figure 4A:
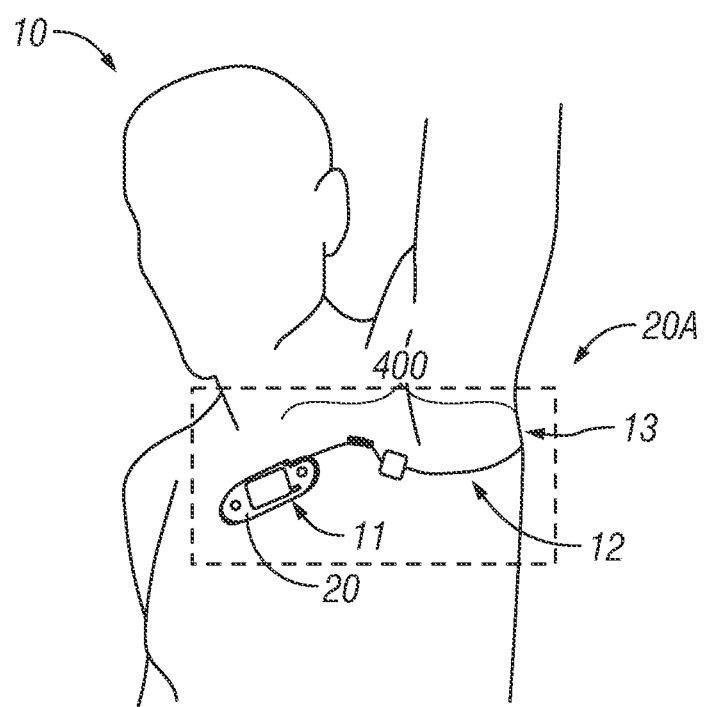
FIG. 4A is a diagram depicting a patient wearing a temperature monitoring system comprising a monitor patch and a temperature probe and configured to measure body temperature of the patient according to certain aspects of the present disclosure.

As indicated above with respect to FIG. 2C, certain embodiments of the monitor patch 20 are configured to operate with external sensors that are in turn configured to produce a signal representative of one or more vital signs of the patient to whom the monitor patch 20 is attached. For example, the second external sensor 234 can be a temperature probe that includes a temperature sensing element (e.g., a thermocouple or thermistor) affixed, either directly or via an interposing layer, to skin of the patient 10 for measuring the patient's body temperature. FIG. 4A is a diagram depicting a patient 10 wearing a temperature monitoring system 20A comprising a monitor patch 20 and a temperature probe 400 that is configured to measure body temperature of the patient 10. In the illustrated example, the temperature probe 400 is configured for axillary temperature sensing of the patient 10 to whom the monitor patch 20 is attached. The monitor patch 20 is attached to the chest 11 of the patient 10, with a sensing portion of the temperature probe 400 retained in the axilla 12 of the patient 10 during body temperature monitoring.

Figure 4B:
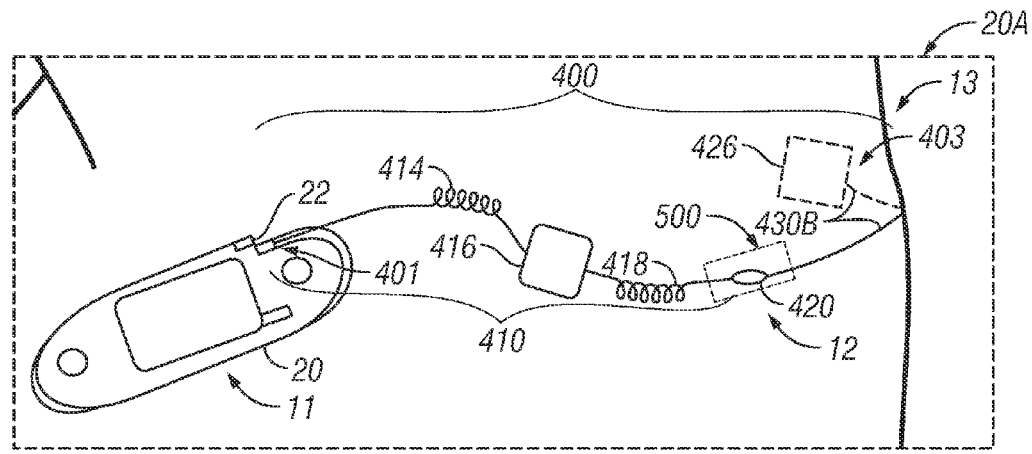
FIG. 4B is a diagram providing an enlarged view of the temperature monitoring system depicted in FIG. 4A according to certain aspects of the present disclosure.

FIG. 4B is a diagram providing an enlarged view of the monitoring system 20A depicted in FIG. 4A according to certain aspects of the present disclosure. As indicated above, the monitor patch 20 is attached to the chest 11 of the patient 10 via, e.g., an adhesive backing (not shown). The temperature probe 400 has a proximal end 401 and a distal end 403 and includes a wiring portion 410, a body connection portion 430B, and a sensing portion 420 disposed between the wiring and body connection portions 410, 430B. The proximal end 401 of the temperature probe 400 is connected to the monitor patch 20 at its connection port 22. In certain embodiments, the proximal end 401 of the temperature probe 400 is removably attached (e.g., plugged) to the monitor patch 20. In other embodiments, the proximal end 401 is fixedly attached (e.g., epoxied or fused) to the monitor patch 20.

Figure 5A:
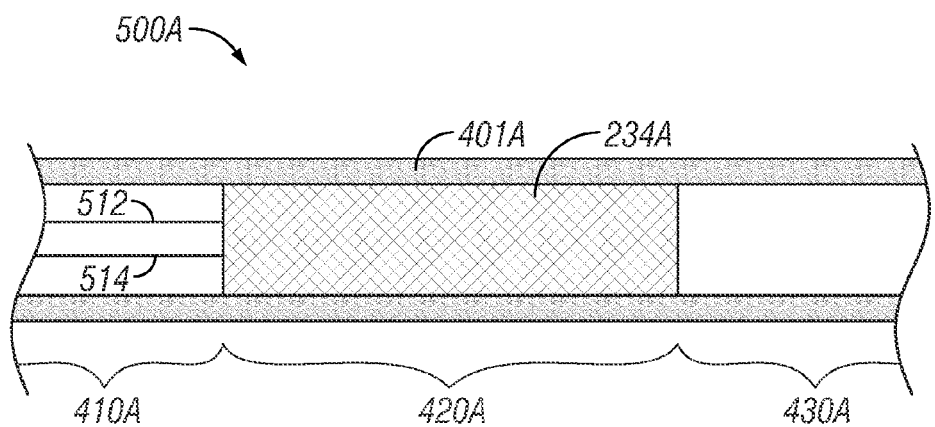
FIGS. 5A-D are diagrams depicting some exemplary embodiments of the temperature probe depicted in FIG. 4B according to alternative aspects of the present disclosure.
Figure 5B:
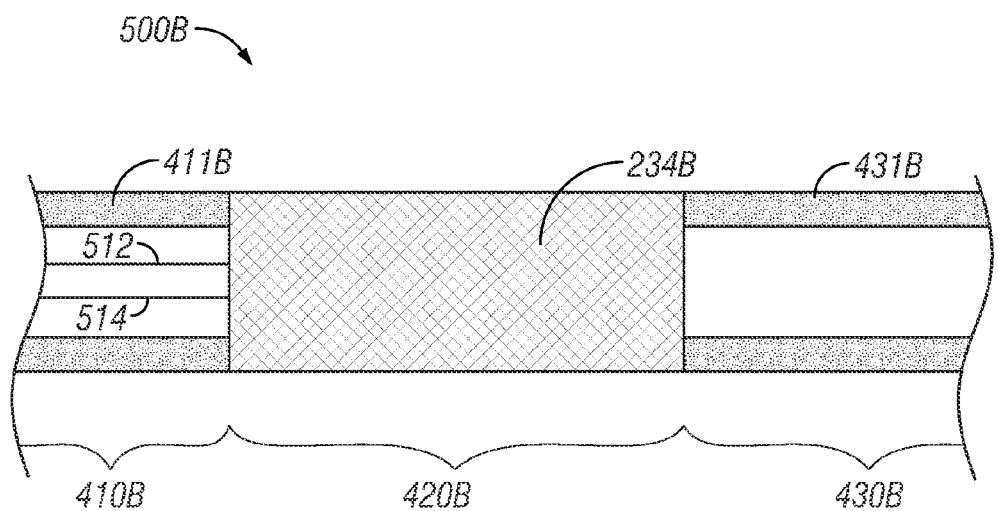
Figure 5C:
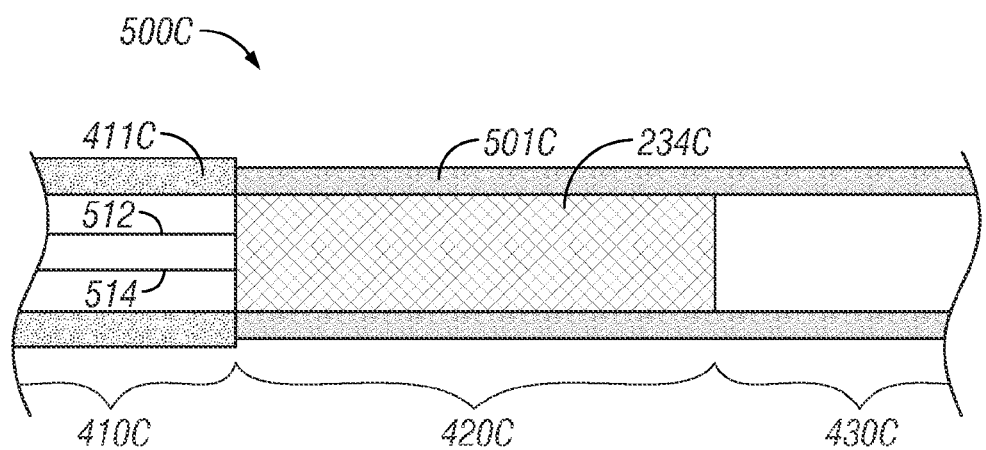
Figure 5D:
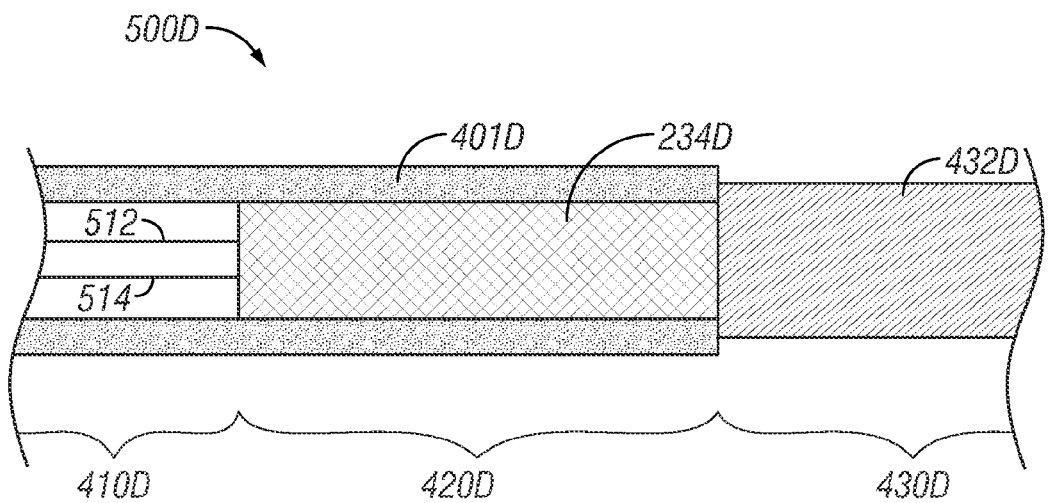
Figure 6A:
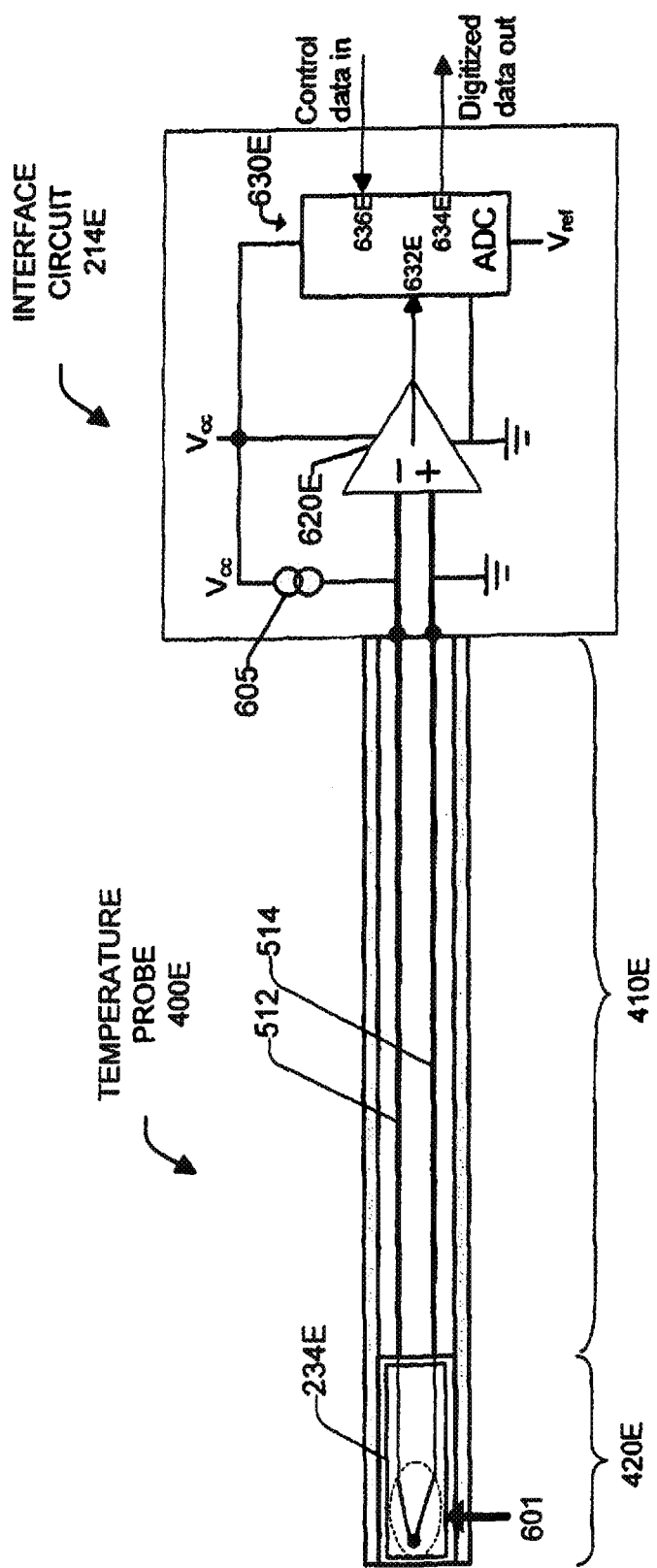
FIGS. 6A-B are diagrams depicting two temperature-sensor interface configurations comprising exemplary temperature probes and sensor interfaces according to alternative aspects of the present disclosure.
Figure 6B:
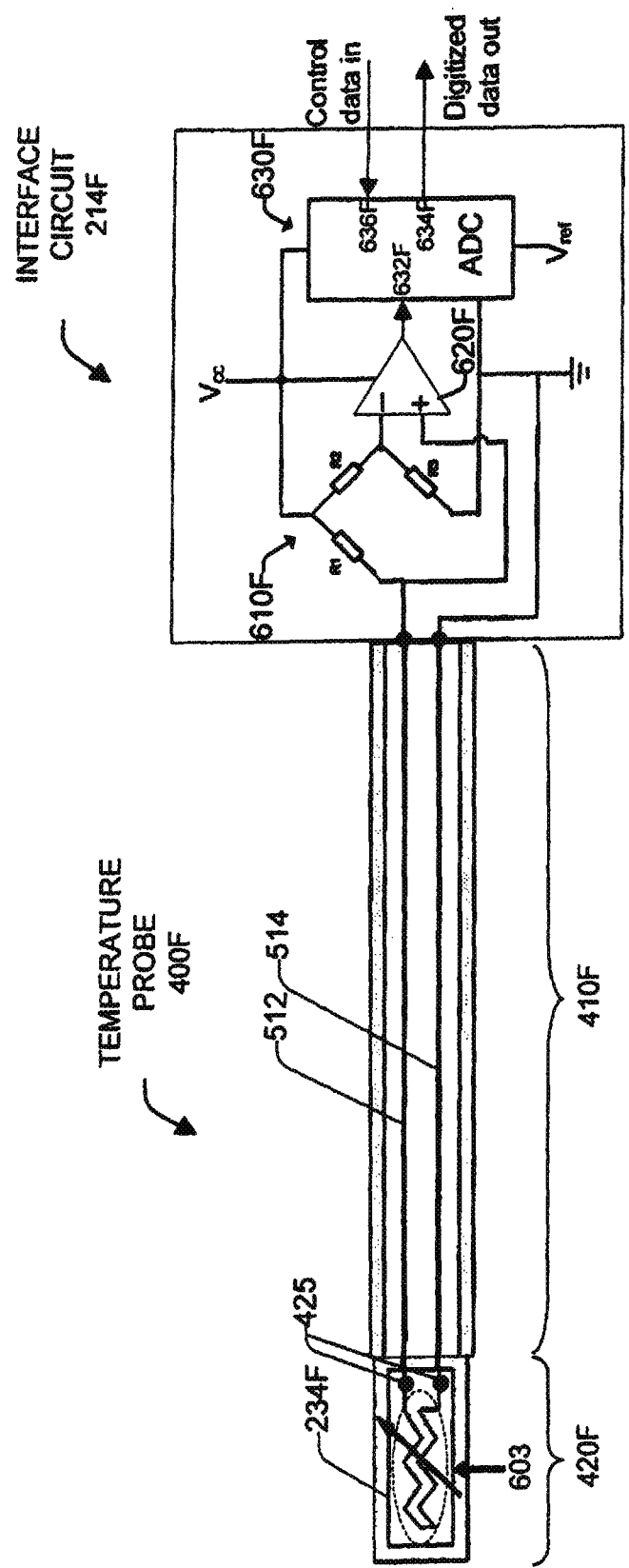

The sensing portion 420 of the temperature probe 400 is configured for placement within the axilla 12 of the patient 10 and includes a temperature sensing element (e.g., 234A-D of FIGS. 5A-D and 234E-F of FIGS. 6A-B). The wiring portion 410 of the temperature probe 400 includes one or more electrical conductors (512, 514 of FIGS. 5A-D and FIGS. 6A-B) for carrying a signal responsive to a change in body temperature of the patient 10 between the temperature sensing element 234 and the monitor patch 20. In the illustrated example of FIG. 4B, the wiring portion 410 includes a flexible cable comprising a tubing and electrical conductors (e.g., a pair of twisted copper wires) placed within the tubing. The wiring portion 410 includes a first coiled section 414 and a second coiled section 418. The coiled sections 414, 418 serve a number of functions including, but not limited to, holding the sensing portion 420 as high as possible in the axilla 12, accommodating arm movements by reducing the "sawing" effect of a straight wire moving along its axis when the patient's arm is moving, creating a wider surface of contact with the skin, thus increasing patient's comfort, creating a contact surface with the skin that does not tend to cause irritation as much as a straight wire would.

In the illustrated example, the monitoring system 20A further includes an adhesive element 416 (e.g., a tape) coupled to the cable between the first and second coiled sections 414, 418 and configured to attach the wiring portion 410 of the cable to the patient's body, e.g., at a point between the chest 11 and the armpit 12 of the patient.

The body connection portion 430B has one end connected to the sensing portion 420 and is configured to be attached to another body portion of the patient 10 such that the sensing portion 420 of the temperature probe 400 can be retained within the axilla 12 of the patient 10. In the illustrated example, such attachment is achieved via an adhesive element 426 (e.g., a tape) coupled to the distal end of the body connection portion 430B. The coupled adhesive element 426 is then attached to a second body portion 13 (e.g., the back of the patient's arm) of the patient 10. In the illustrated embodiment of FIG. 4B, the body connection portion 430B includes an elastic tubing comprising an elastic polymers (elastomers) such as natural rubber, synthetic polyisoprene, butyl rubber, and the like. In such embodiments, the adhesive element 426 is attached to the patient's body while the elastic tubing is in its stretched state such that the restorative ("pulling") tensile force in the stretched tubing helps to hold the temperature sensing portion 420 in place within the axilla 12 of the patient. The adhesive elements 416, 426 can be pre-attached adhesive tabs with a peel-off backing. Alternatively, the adhesive elements 416, 426 can be pre-attached fixture tab that allow for the use of a standard medical tape. Openings (holes, slots, etc.) can be present in both cases to allow skin to breathe. The adhesive elements 416, 426 are preferably positioned at about the same vertical level, high enough so both of the stretchable coiled sections 414, 418 would pull the sensing portion 420 upward.

Figure 4C:
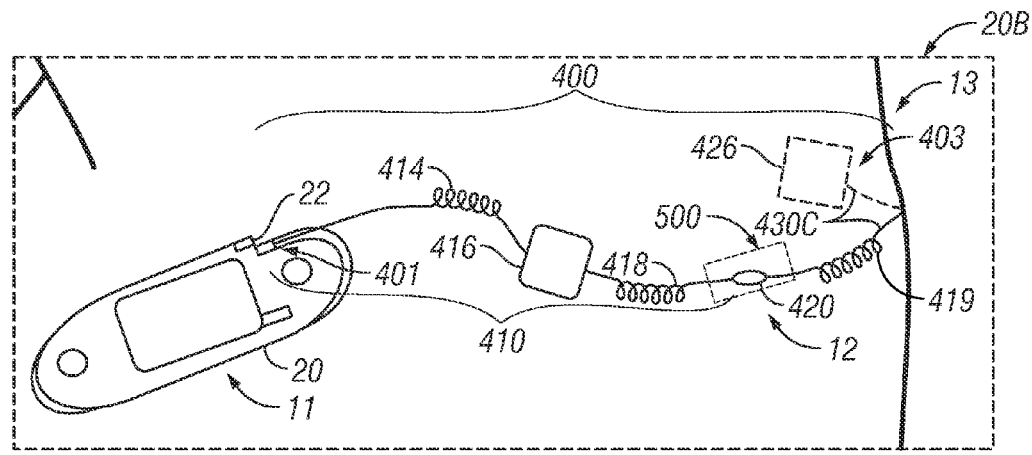
FIG. 4C is a diagram providing an enlarge view of an alternative monitoring system according to certain aspects of the present disclosure.

FIG. 4C is a diagram providing an enlarged view of an alternative monitoring system 20B according to certain aspects of the present disclosure. The monitoring system 20B is substantially the same as the monitoring system 20A, except an additional (e.g., third) coiled section 419 is provided in body connection portion 430C in place of the elastic tubing 430B. The additional coiled section 419 can provide all or some of the pulling force such as the one provided by the elastic tubing in the embodiment of FIG. 4B. In one or more implementations, the coiled section 419 acts as a spring. The remainder of the body connection portion 430C may include an elastic or inelastic flexible tubing.

Figure 4D:
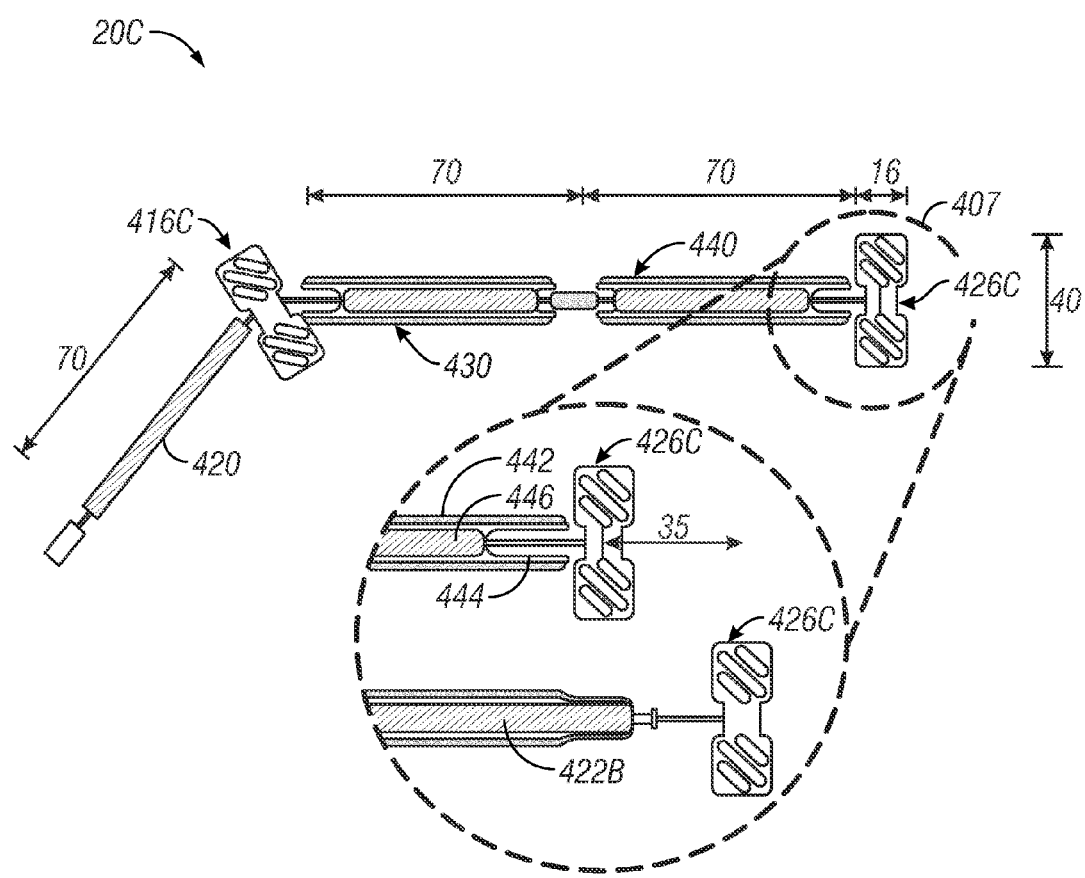
FIG. 4D is a diagram depicting another alternative monitoring system according to certain aspects of the present disclosure.

FIG. 4D is a diagram depicting another alternative monitoring system 20C according to certain aspects of the present disclosure. The monitoring system 20C includes a first stretchable component 420, a second stretchable component 430, and a third stretchable component 440. The monitoring system 20C further comprises adhesive elements 416C, 426C. At least some of the stretchable components (e.g., 440) include a tubing 442 with a flexible boot 424 at the end thereof as illustrated by an enlarged view of an end section 407 of the stretchable component 440. The enlarged view shows the stretchable component 440 in its unstretched state (top) and in its stretched state (bottom). The adhesive elements 416C, 426C are substantially similar to the adhesive elements 416, 426 described above with respect to the monitoring system 20A. The adhesive element 426C depicted in the enlarged view include slotted holes that allow skin to breathe.

A multitude of modifications and additions to the illustrated embodiments of FIGS. 4B, 4C and 4D are possible without departing from the scope of the disclosure. For example, the body connection portion 430 of the temperature probe 400 can include one or more coiled sections similar to the coiled section 414 of the wiring portion 410. Any or all of the coiled sections 414, 418, 419 in the embodiments of FIGS. 4B and 4C may be replaced with elastic elements (e.g., elastic tubing). The adhesive element 416 may be coupled to the body connection portion 430 at a point different than the distal end of the body connection portion 430. In certain embodiments, entirely different means of attaching the body connection portion 430 to the patient's body may be used. For example, the body connection portion 430 may itself be in the form of an adhesive tape that can stick to the body of the patient 10 or may include an elastic loop (e.g., a rubber band) to be placed around the patient's arm.

While the temperature probe 400 in the illustrated embodiments of FIGS. 4A-C is shown to be operatively coupled to a vital-sign monitor patch worn by the patient 10, the temperature probe 400 may be alternatively operatively coupled to other types of monitoring devices such as a stationary monitoring unit located near the patient's hospital bed. Such a stationary monitoring unit can take readings of the patient's body temperature based on a signal from the temperature probe 400 and send the temperature readings to a surveillance server via a wired or wireless connection and make other decisions such as providing an indication of an alarm condition (e.g., a high body temperature condition or a loss of thermal contact between the temperature probe and the patient).

FIGS. 5A-D are diagrams depicting various exemplary embodiments of the temperature probe according to alternative aspects of the present disclosure. For the purposes of illustration only, without an intent to limit the scope of the present disclosure in any way, the embodiments will be described with references to elements of FIG. 4B. For clarity, each of the diagrams focuses on a region 500A-D (corresponding to region 500 in FIG. 4B) of the thermocouple 400 where sensing portion 420A-D interfaces with wiring portion 410A-D and body connection portions 430A-D. The figures are not drawn to scale.

In the first exemplary embodiment of the temperature probe 400 depicted in FIG. 5A, the wiring portion 410A, the sensing portion 420A, and the body connection portion 430A comprise a single hollow flexible cable 401A. The wiring portion 410A of the flexible cable 401A includes a first electrical conductor 512 and a second electrical conductor 514. The sensing portion of the flexible cable 401A houses a temperature sensing element 234A that is electrically connected to the first and second electrical conductors 512, 514. The temperature sensing element 234A is configured to make thermal contact with the axilla of the patient 10 through the surrounding flexible cable 401A. In the illustrated example, the body connection portion 430A of the flexible cable 401A is empty inside.

In the second exemplary embodiment of the temperature probe 400 depicted in FIG. 5B, the wiring portion 410B comprises a first hollow flexible cable 411B having a first electrical conductor 512 and a second electrical conductor 514. The sensing portion 420B includes a temperature sensing element 234B. In the illustrated example, the temperature sensing element 234B is mechanically connected (e.g., glued or fused) to an end portion of the first flexible cable 411B and is electrically connected to the first and second electrical conductors 512, 514. The temperature sensing element 234B is configured to make a direct physical and thermal contact with the axilla 12 of the patient 10 (i.e., not through a flexible cable). The body connection portion 430B comprises a second hollow flexible cable 431B. In the illustrated example, the second flexible cable 431B is empty inside.

In the third exemplary embodiment of the temperature probe 400 depicted in FIG. 5C, wiring portion 410C comprises a first flexible cable 411C having a first electrical conductor 512 and a second electrical conductor 514. The sensing portion 420C and body connection portion 430C comprise a second hollow flexible cable 501C. The second flexible cable 501C is mechanically connected (e.g., glued or fused) to an end portion of the first flexible cable 411C. The sensing portion 420C of the second flexible cable 501C houses a temperature sensing element 234C that is electrically connected to the first and second electrical conductors 512, 514. The temperature sensing element 234C is configured to make a thermal contact with the axilla of a patient through the surrounding second flexible cable 501C. The body connection portion 430C of the second flexible cable 401C is empty inside.

In the fourth exemplary embodiment of the temperature probe 400 depicted in FIG. 5D, the wiring portion 410D and the sensing portion 420D comprise a first flexible cable 401D. The wiring portion 410D of the first flexible cable 401D includes a first electrical conductor 512 and a second electrical conductor 514. The sensing portion 420D of the first flexible cable 401D houses a temperature sensing element 234D. The temperature sensing element 234D is electrically connected to the first and second electrical conductors 512, 514. The body connection portion 430D comprises a flexible tape 432D that is mechanically connected (e.g., glued or fused) to the sensing portion 420D at the temperature sensing element 234D and/or an end portion of the first flexible cable 401D. In certain embodiments, the flexible tape 432D includes an adhesive section that can be attached to a body portion (e.g., the back of the patient's arm) so as to retain the sensing portion 420D of the temperature probe 400 within the axilla 12 of the patient 10.

The above embodiments of FIGS. 5A-5D are exemplary only, as other embodiments can be employed without departing from the scope of the present disclosure. For example, a modular arrangement in which the cables are snap connectable with the temperature sensing element can be employed, as well as other physical configurations.

FIGS. 6A-B are diagrams depicting two temperature-sensor interface configurations comprising exemplary temperature probes 400E, 400F and sensor interfaces 214E, 214F according to alternative aspects of the present disclosure. Each of the temperature probes 400E, 400F comprises respective wiring portion 410E, 410F and sensing portion 420E, 420F having temperature sensing element 234E, 234F. Each of the sensor interface circuits 214E, 214F is connected to the temperature probe 400E, 400F and configured to receives a sensor signal from the temperature sensing element 234E, 234F via electrical conductors 512, 514 in the wiring portion 410E, 410F of the probe 400E, 400F. As described above with respect to FIG. 2, the sensor interface 214E, 214F is part of a processing and sensor interface module (e.g., 201) of a vital-sign monitor patch (e.g., 20). For simplicity, each of the diagrams shows only a wiring portions 410E, 410F and a sensing portion 420E, 420F of the temperature probe 400E, 400F. The figures are not drawn to scale.

In the first exemplary probe-sensor interface configuration depicted in FIG. 6A, the temperature sensing element 234E is a thermocouple that comprises a junction 601 between two different metals. The junction 601 produces a voltage difference related to temperature at the junction 601. The junction is of dissimilar metals including specific alloys such as platinum and platinum-rhodium alloy (Type S) or chromel and alumel (Type K). This embodiment of a thermocouple is exemplary only, as other embodiments may be employed. For example, additional circuits/elements relating to cold junction compensation may be used. In some embodiments, the temperature sensing element may comprise a resistance temperature detector (RTD) based on platinum.

A signal representative of the voltage difference produced at the junction 601 of the thermocouple 234E is received by the sensor interface 214E via the first and second electrical conductors 512, 514 in the wiring portion 410E. The sensor interface 214E includes an amplifier 620E, an analog-to-digital converter (ADC) 630E and a current source 605. The current source 605 supplies a constant DC current that flows through the junction and produces a signal representative of the voltage difference across the junction. The signal is received at the minus input of the amplifier 620E. The received signal is amplified by the amplifier 620E, and the amplified signal is received by the ADC 630E at input port 632E. The ADC 630E digitizes the amplified signal and provides a stream of digitized data at output port 634E. The stream of digitized data is passed to a processor (e.g., 202 of FIG. 2) for further processing and/or transmission to a surveillance server (e.g., 60 of FIG. 1) via a bride (e.g., 40 of FIG. 1). In certain embodiments, the ADC 630E at its control data input port 636E receives from the processor a set of control data that configures one or more functionalities of the ADC 630E including, not limited to, its sampling (digitization) rate and dynamic range.

In the second exemplary probe-sensor interface depicted in FIG. 6B, the temperature sensing element 234F includes a thermistor 603, a type of resistor whose resistance varies with temperature. The thermistor 603 can be made from a material that has a positive temperature coefficient (PTC) (called a "PTC thermistor") or from a material that has a negative temperature coefficient (NTC) (called a "NTC thermistor").

Two electrical contacts 425 of the thermistor 603 are connected to the sensor interface circuit 214F via the first and second electrical conductors 512, 514 in the wiring portion 410F. The sensor interface circuit 214F includes a Wheatstone bridge 610F having three fixed resistors (R1, R2, and R3), an amplifier 620F, and an analog-to-digital converter (ADC) 630F. By the connection provided by the first and second electrical conductors 512, 514, the thermistor 603 functions as a fourth and variable resistor in the Wheatstone bridge 610F such that the bridge 610F outputs a signal that is responsive to a change in the resistance of the thermistor 603, which resistance is in turn responsive to a change in the body temperature of the patient 10. The signal generated at the Wheatstone bridge 610 is received by an amplifier 620F. An amplified signal at the output of the amplifier 620F is received by an input port 632F of the ADC 630F. The ADC 630F digitizes the received signal and provides a stream of digitized data at output port 634F. The stream of digitized data is passed to a processor (e.g., 202 of FIG. 2) for further processing and/or transmission to a surveillance server (e.g., 60 of FIG. 1). In certain embodiments, the ADC 630F at its control data input port 636F receives a set of control data that configures one or more functionalities of the ADC 630F including, not limited to its sampling (digitization) rate and dynamic range.

With references to FIGS. 1, 2 and 4A-B, the monitor patch 20 worn by the patient 10 receives a signal from a temperature sensing element (e.g., a thermocouple and a thermistor) of the temperature probe 400, the signal responsive to a change in body temperature of the patient 10. The signal is amplified and digitized into a stream of data by the sensor interface circuit 214 as explained above with respect to FIGS. 6A-B. The digitized signal is then received by the processor 202. The processor 202 generates a sequence of temperature readings based on the digitized signal. The processor 202 is operatively connected to a wireless communication system (e.g., the wireless transceiver 207) which transmits data indicative of the patient's body temperature to the surveillance server 60 via the bridge 40. In certain embodiments, the processor 202 performs a number of temperature monitoring functions on the temperature readings to determine, inter alia, a high temperature condition and occurrence and loss of thermal contact between the patient 10 and the temperature probe 400.

Figure 7:
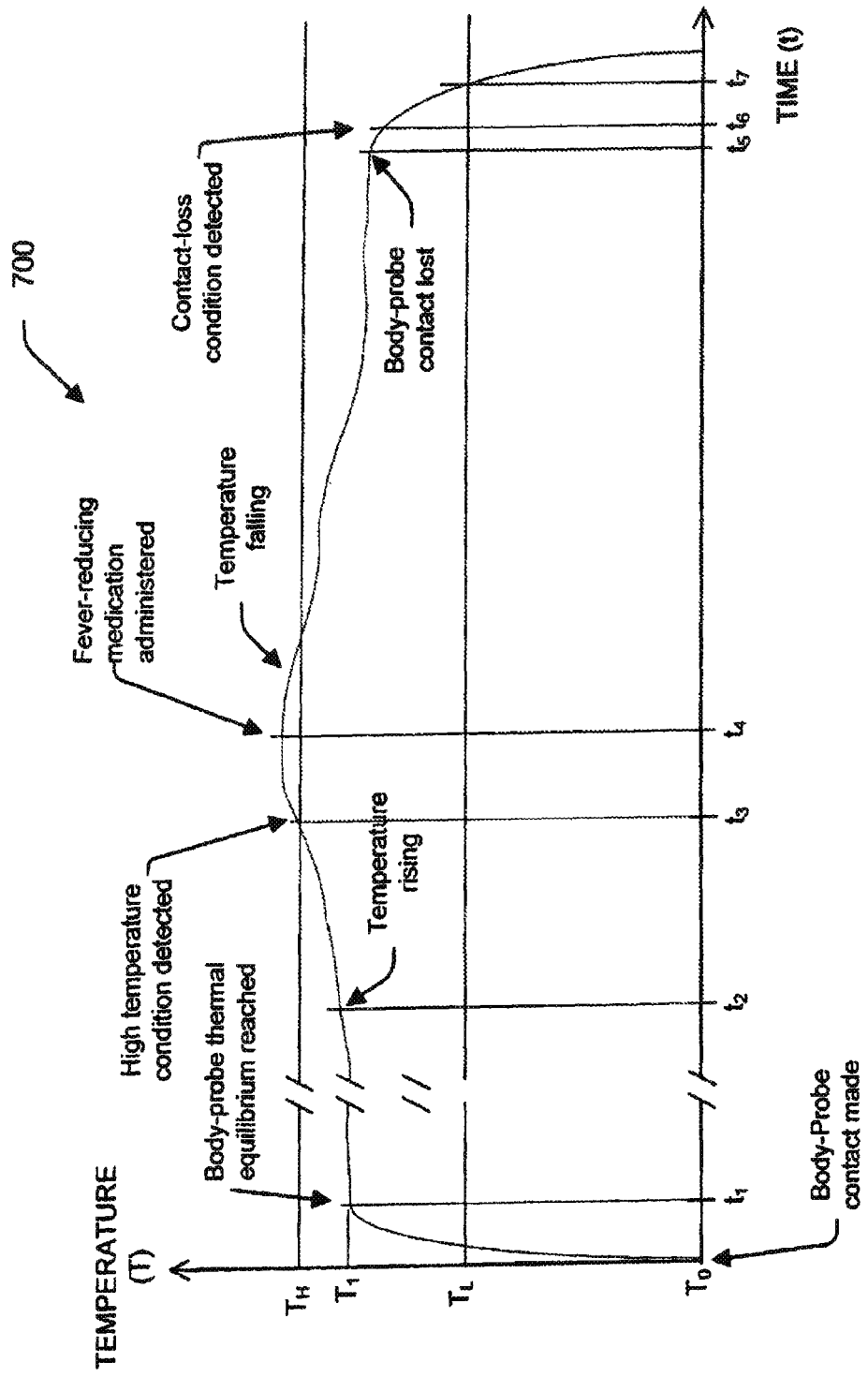
FIG. 7 is a graph of a measured temperature reading versus time for illustrating an exemplary temperature monitoring scheme according to certain aspects of the present disclosure.

FIG. 7 is a graph 700 of a measured temperature reading (T) versus time (t) for illustrating an exemplary temperature monitoring scheme according to certain aspects of the present disclosure. The graph 700 shows a low temperature limit ($T_L$) and a high temperature limit ($T_H$) that are used in the temperature monitoring scheme. For the purposes of illustration only without an intent to limit the scope of the present disclosure in any way, the exemplary temperature monitoring scheme will be described with reference to elements of FIGS. 4A,B. At t=0, a body-probe contact between the body of the patient 10 and the temperature probe 400 is made, e.g., by securing the sensing portion 420 of the temperature probe 400 within the axilla 12 of the patient 10. A processor (the processor 202 of FIG. 2) executing a control program in the monitoring device (e.g., the monitor patch 20) can recognize the body-probe contact by a number of different ways. For example, the recognition can be achieved from the temperature reading rising sharply past the low temperature limit ($T_L$) at a rate exceeding a first threshold rate of rise after having been below $T_L$ at least once.

As seen in FIG. 7, the temperature reading rises from an initial (e.g., open-air) value ($T_0$) at $t=t_1$ to an equilibrium value ($T_1$) at $t=t_1$ when the temperature sensing element has reached a thermal equilibrium with the patient's body.

At $t=t_2$, the temperature reading begins to rise, indicating that the patient's body temperature is on the rise. At $t=t_3$, the temperature reading exceeds the high temperature limit ($T_H$). When this occurs, the processor executing control software in the monitoring device can invoke a high temperature handler routine in the control software and take a number of predetermined actions. For example, the processor can cause the transmitter 209 (FIG. 2) to start sending a signal indicative of the high temperature alarm condition to the surveillance server 60 either directly or via the bridge 40. In response, the surveillance server 60 can send a notification to a hospital system (e.g., the workstation 100 of FIG. 1). The monitor patch 20 can also set off an alarm, e.g., at the monitor patch 20 or at a stand alone monitoring unit or at a hospital system (e.g., the workstation 100 of FIG. 1), thereby notifying a nurse or other caregiver. The monitor patch 20 can enter into an alert operation mode from the normal operation mode and take and transmit the temperature readings (e.g., to the surveillance server 60) at a faster rate. For instance, the monitor patch 20 can take and transmit the temperature reading every 10 minutes during the normal operation mode, but does so every 2 minutes in the alert operation mode. In certain embodiments, the temperature monitoring scheme utilizes two high temperature limits ($T_{H1}$ and $T_{H2}$, where $T_{H2} > T_{H1}$) and different sets of predetermined actions are performed depending on whether the temperature reading has exceeded only $T_{H1}$ or both $T_{H1}$ and $T_{H2}$.

In the illustrated example of FIG. 7, it is assumed that at $t=t_4$, a nurse who has been notified of the high temperature condition of the patient 10 has decided to administer a fever-reducing medication to the patient 10. Responding to the fever-reducing medication, the patient's body temperature reading begins to fall gradually and reach a relatively stable level below $T_H$.

However, at $t=t_5$, the body-probe contact is lost due to, e.g., the patient 10 opening the arm in a manner that causes the sensing portion 420 of the temperature probe 400 to be detached from the axilla 12 of the patient 10, or the temperature probe 400 accidentally falls off the patient's body. The loss of body-probe contact causes the temperature reading to fall towards a lower (e.g., open-air) value at a relatively sharp rate of decline. In certain embodiments of the temperature monitoring system 20A, the processor executing control software in the monitor patch 20 can detect the loss of body-probe contact by computing a rate of decline in the sequence of temperature readings and comparing the computed rate of decline to a threshold rate of decline. If the rate of decline exceeds the threshold rate of decline for a predetermined number of samples (e.g., 1-4), the processor determines that the body-probe contact has been lost and generates an indication of the loss of contact. In the illustrated example of FIG. 7, the loss of body-probe contact is detected at $t=t_6$. As can be seen from FIG. 7, the detection scheme based on the rate of decline described herein can detect the loss of contact earlier than a scheme relying on the temperature readings falling below the low temperature limit ($T_L$). The latter scheme would not detect the loss of contact until $t=t_7$.

In certain embodiments, an indication of the loss of contact is wirelessly transmitted to the bridge 40 to be sent to the surveillance server 60, and the surveillance server 60 then provides a notification of the loss of contact to a hospital system (e.g., the workstation 100 of FIG. 1). In other embodiments, in addition or in lieu of the wireless transmission of the indication, the monitor patch 20 itself may sound an alarm indicating the loss of contact to the patient 10 or a nurse or caregiver who is near the patient 10.

In certain embodiments, the monitor patch 20, after providing the indication, enters a sleep mode in which no additional temperature readings are taken. Alternatively, the monitor patch 20 can continue to take additional temperature readings to determine whether a new body-probe contact has been established.

Figure 8A:
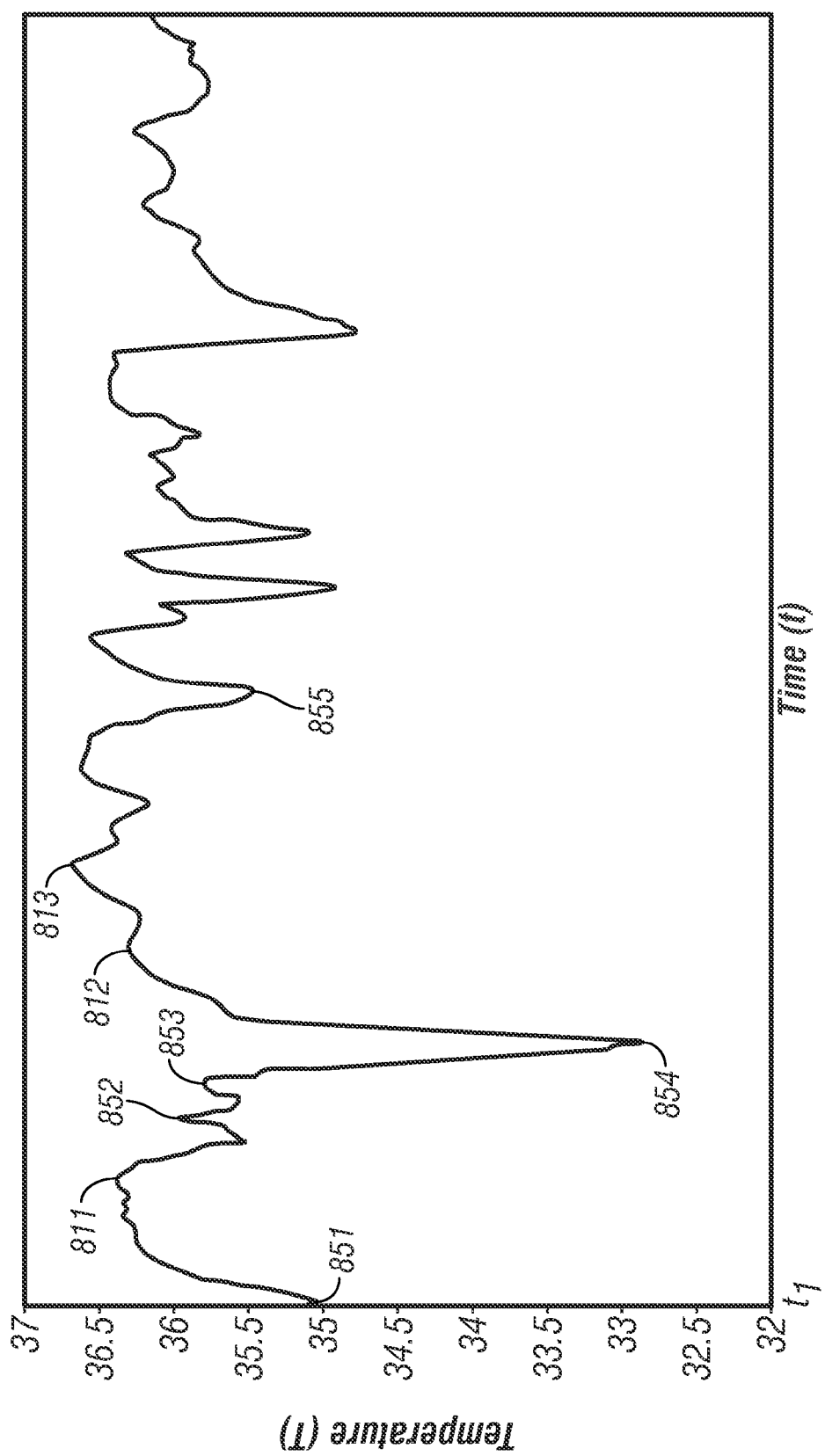
FIG. 8A is diagram depicting a realistic temperature reading (T) versus time (t) graph associated with a temperature monitoring system according to certain aspects of the present disclosure.

FIG. 8A is diagram depicting a realistic temperature reading (T) versus time (t) graph 800A associated with a temperature monitoring system (e.g., 20) according to certain aspects of the present disclosure. The temperature readings have peaks (e.g., 811, 812) and valleys (e.g., 854, 855). The up-and-down fluctuations in the temperature readings can be caused by movements of a patient's arm (up and down/back and forth), for example. This is because arm movements can affect the quality of thermal contact between the sensing portion 420 of the temperature probe 400 and the axilla 12 of the patient 10. In general, when the temperature readings are rising rapidly as between reading 854 and reading 812, the rise may be attributable to a transition from a relatively poor thermal contact to a good thermal contact, e.g., by armpit closing. On the other hand, when the temperature readings are decreasing rapidly as between reading 853 and reading 854, the decrease may be attributable to a transition from a relatively good thermal contact to a poor thermal contact caused, e.g., by armpit opening up or the temperature probe being detached from the patient 10, thereby partially or fully exposing the sensing portion 420 to ambient air. A reading taken while the quality of thermal contact is poor is likely to be inaccurate, and thus it is desirable to identify occurrence of such a poor thermal contact so that inaccurate readings associated with the poor thermal contact may be rejected, and only valid temperature readings associated with a good thermal contact are reported, e.g., to the surveillance server 60. In addition, a prolonged loss of thermal contact may be detected and reported so that the patient 10 and/or a caregiver can be alerted. As used herein, the term "poor thermal contact" refers to partial or complete loss of contact between a temperature probe and a person to whom the temperature probe is supposed to be attached.

In certain aspects of the present disclosure, the monitoring system 20 achieves these objectives by adopting the following principles:
1) Only maximum readings (peaks or plateaus) are considered as potentially valid readings.
2) Temperature readings on a downward slope are considered to be associated with a poor thermal contact.
3) Given an almost impossible rate of decay of the core body temperature (e.g., –2 C/h), any peak or plateau below this threshold decay rate are rejected.

Applying these principles, a current (new) temperature reading ($T_{NEW}$) is reported as a new valid temperature reading and replaces the current maximum temperature reading ($T_{MAX}$) if $T_{NEW}$ fulfills at least one of the following acceptance conditions:

Condition 1: Initial stabilization is just completed;
Condition 2: ($T_{NEW} > T_{MAX}$); or
Condition 3: ($T_{NEW} < T_{MAX}$) AND a peak/plateau (e.g., a local maximum) is detected AND a gradient condition, namely, the peak/plateau is at or above a threshold decay curve representing the threshold decay rate (e.g., e.g., –2 C/h), is satisfied.

Conversely, if the current temperature reading fails to satisfy all of these conditions, the reading is considered inaccurate and rejected, and the monitoring system 20 retains the current $T_{MAX}$ as the currently effective temperature reading value.

Figure 8B:
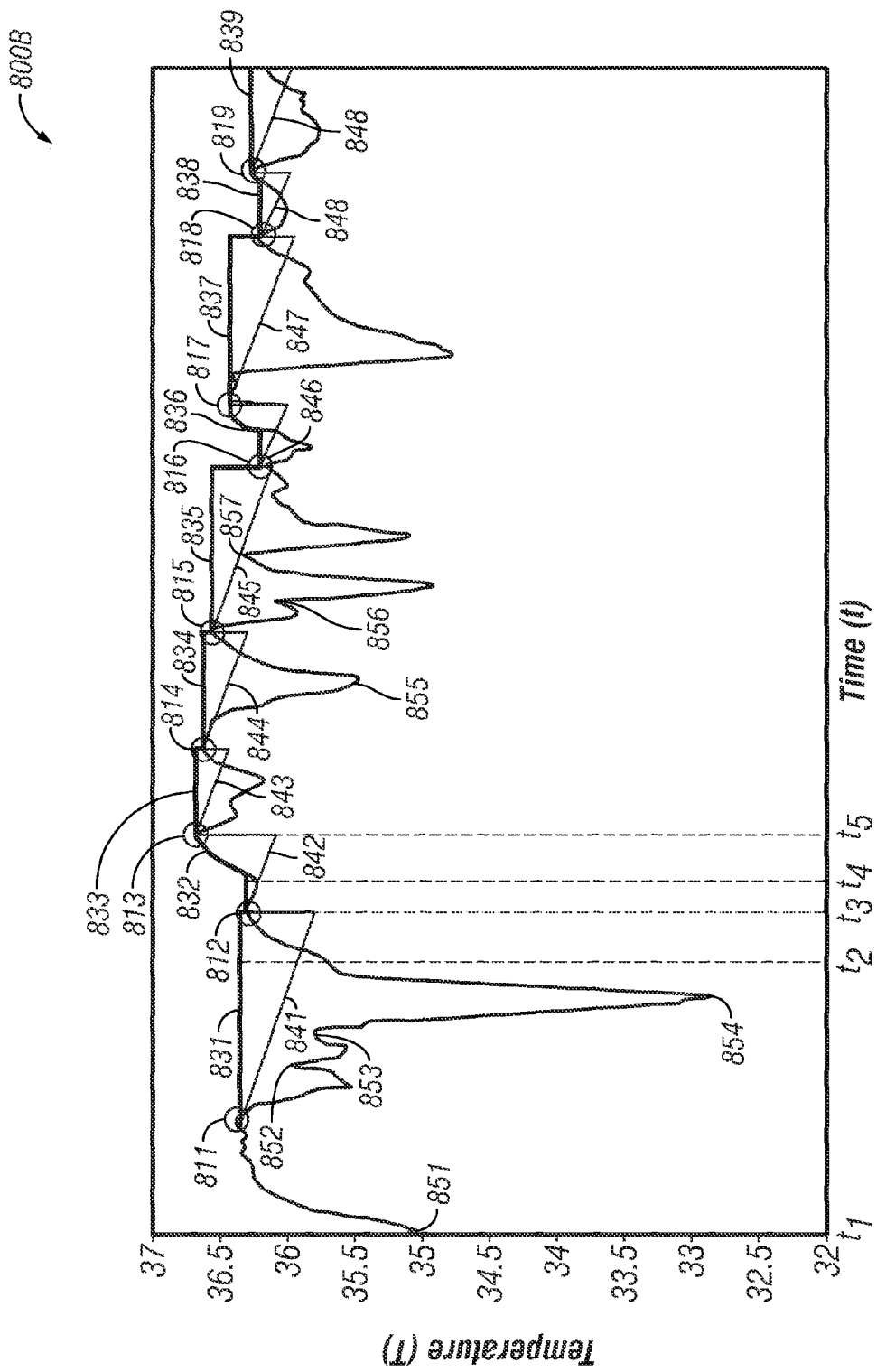
FIG. 8B shows a graph illustrating an exemplary temperature monitoring algorithm based on certain acceptance conditions according to certain aspects of the present disclosure.
Figure 9:
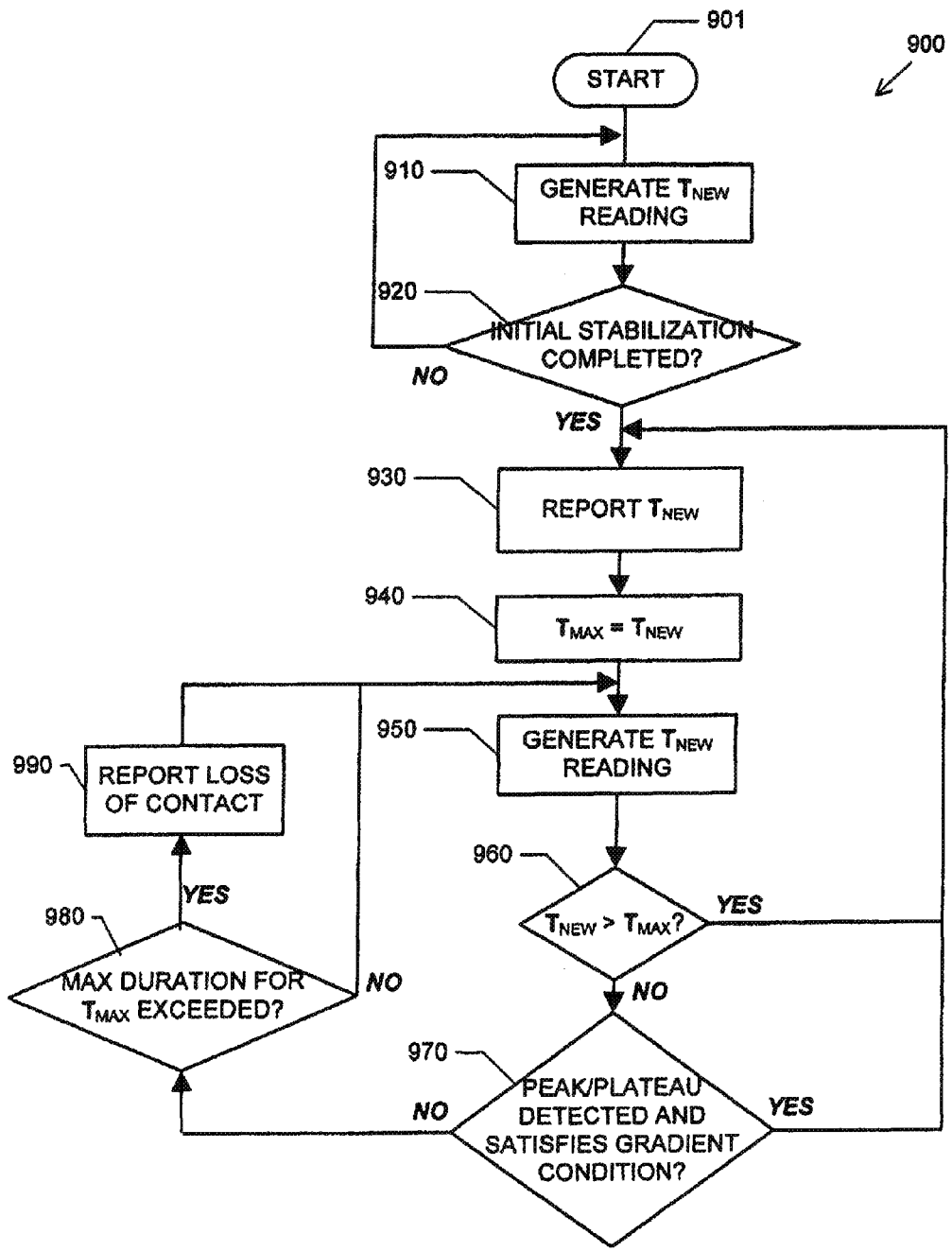
FIG. 9 is a flowchart illustrating an exemplary process associated with the exemplary temperature monitoring algorithm of FIG. 8B according certain aspects of the present disclosure.

FIG. 8B shows a graph 800B graphically illustrating an exemplary temperature monitoring algorithm based on the above-enumerated acceptance conditions according to certain aspects of the present disclosure. FIG. 9 is a flowchart illustrating an exemplary process 900 associated with the exemplary temperature monitoring algorithm of FIG. 8B according certain aspects of the present disclosure. Indicated on the graph 800B are peak temperature readings (e.g., in between 811-819) that satisfy at least one of Conditions 1-3 enumerated above. Lines (straight or curvilinear) 831-839 represent currently effective temperature reading values, e.g., the values that the monitoring system 20 considers as the current axillary temperature of the patient 10. Saw-tooth-shaped curves 841-849 represent threshold decay curves generated based on a threshold decay rate (e.g., e.g., –2 C/h) discussed above with respect to Condition 3.

The algorithm 900 begins at start state 901 and proceeds to operation 910 in which a new temperature reading ($T_{NEW}$) is generated. By way of example, the $T_{NEW}$ reading can be generated by a processor of the monitor patch 20 based on a signal generated by a temperature sensing element (e.g., 234A-D of FIG. 5A-D) of the temperature probe 400. As described above, the sensing element can be a thermocouple (234E of FIG. 6A), thermistor (234F of FIG. 6B) or any another temperature transducer configured to generate a signal responsive to a change in body temperature of a person to whom the temperature probe 400 is attached.

The algorithm 900 proceeds to decision state 920 in which a query is made as to whether an initial stabilization (e.g., a thermal equilibrium) has been completed for the temperature readings, e.g., after an initial attachment of the temperature probe 400 to the patient 10 or after a prolonged loss of thermal contact. This query is designed to determine whether the current $T_{NEW}$ reading satisfies Condition 1, e.g., whether the monitoring has gone through or completed its stabilization phase.

In certain embodiments, the decision state 920 can involve, for example, determining whether the current and recent temperature readings have flattened out after a sharp increase by monitoring a slope (e.g., derivative) or an average of slopes of the temperature readings versus time. In other embodiments, the decision state 920 can involve waiting for a certain period of time (e.g. 15 minutes) before reporting a value, even though some peaks or plateaus might be found. After that stabilization period, the maximum value found will be reported as the first value. The purpose of the stabilization period is to reduce chances of having low peaks of temperature being reported right after system activation because of the fact that the gradient criterion cannot be applied (gradient criterion requires an initial value). For example, if a peak is found after activation, without the gradient criterion to discard it, it would be reported as a valid reading. Waiting 15 minutes and taking the maximum value offers better chances of starting with a more accurate value. The above examples illustrate simple stabilization algorithms (e.g., waiting Z minutes and taking the maximum peak/plateau value). There can be different methods of obtaining a first reading such as using a predictive algorithm.

If answer to the query a the decision state 920 is NO, (initial stabilization not completed), the process 900 loops back to the operation 910 in which another $T_{NEW}$ reading is generated. On the other hand, if answer to the query at the decision state 920 is YES (initial stabilization completed), the process 900 proceeds to operation 930 in which the new temperature reading ($T_{NEW}$) is reported, and to operation 940 in which the $T_{NEW}$ reading is assigned to $T_{MAX}$. In the illustrated example of FIG. 8B, a first temperature reading 851 is taken at time 801, e.g., after an initial attachment of the temperature probe 400 to the patient 10, and an initial stabilization is determined to be completed at reading 811.

The process 900 then proceeds to operation 950 in which another $T_{NEW}$ reading is generated and then to decision state 960 in which a query is made as to whether the $T_{NEW}$ reading obtained at the operation 950 is larger than the current maximum temperature reading ($T_{MAX}$), which at this point is equal to the value of the initially-stabilized temperature reading 811. This query is designed to determine whether the current $T_{NEW}$ reading satisfies Condition 2, namely $T_{NEW} > T_{MAX}$. If answer to the query is YES ($T_{NEW} > T_{MAX}$) the process 900 loops back to the operations 930 and 940 in which the current $T_{NEW}$ reading is reported and assigned to $T_{MAX}$.

On the other hand, if the answer to the query at the decision state 960 is NO ($T_{NEW} \leq T_{MAX}$), the process 900 proceeds to decision states 970 in which a first query is made as to whether the new temperature reading corresponds to a peak (e.g., local maximum) or a plateau (e.g., relatively flat region after a local maximum), and, if so, a second query is made as to whether the peak/plateau satisfies the gradient condition, namely, whether the peak/plateau is at or above a corresponding one of the threshold decay curves 841-849 representing the threshold decay rate (e.g., −2 C/h). The first and second queries of the decision state 970 are designed to determine whether the current $T_{NEW}$ reading satisfies Condition 3. In certain embodiments, the first query relating to the occurrence of a peak/plateau involves obtaining a sequence of temperature readings and retroactively identifying one of the readings corresponding to a local maximum. If the first and second queries of the decision state 970 are both satisfied (YES), the process 900 loops back to the operations 930 and 940 in which the current $T_{NEW}$ reading is reported and assigned to $T_{MAX}$.

On the other hand, if at least one of the first and second queries is not satisfied (NO), the process 900 proceeds to another decision state 980 in which a query is made as to whether a maximum duration for the current $T_{MAX}$ reading has been exceeded. This query detects a prolonged loss of thermal contact between the temperature probe 420 and the axilla 12 of the patient 10. In certain exemplary embodiments, the maximum duration is preset at a value between about 10 and 30 minutes. If the query at the decision state 980 is NO (maximum duration not exceeded), the process 900 loops back to the operation 950 where another temperature reading is generated and then to decision state 960 and potentially to decision state 970 where Conditions 2 and 3, respectively, are checked. The algorithm maintains the current $T_{MAX}$ reading, and the monitoring system 20 considers it as the currently effective temperature reading as indicated by the line 831.

On the other hand, if the answer to the query at the decision state 980 is YES (maximum duration exceeded), the process 900 proceeds to operation 990 in which the loss of thermal contact is reported (e.g., displayed on hospital system 100) and then back to operations 950, where a next $T_{NEW}$ reading is taken.

In the illustrated example of FIG. 8B, temperature readings (e.g., 852, 853) generated after the reading 811 do not satisfy the combination of first and second queries of the decision state 970, and the maximum duration for the current $T_{MAX}$ reading is exceeded at $t_2$. The monitoring system 20 at or after $t_2$ reports the prolonged loss of thermal contact to, e.g., a database in the surveillance server 60 or the patient 10 and/or nurse/caregiver at operation 990. After the reporting at operation 990, the process 900 loops back to the operations 950, where a next $T_{NEW}$ reading is taken.

After determining (e.g., identifying) the initially-stabilized $T_{NEW}$ reading 812, the process 900 detects a series of new peak temperature readings 813-819 that satisfies Condition 2 (813, 817, 819) or Condition 3 (814, 815, 816, 818). Other $T_{NEW}$ readings, such as readings 852, 853, 856, however, are rejected because they do not satisfy either Condition 2 ($T_{NEW}$ not greater than the current $T_{MAX}$ 815) or Condition 3 ($T_{NEW}$ below the threshold decay curve 845). Valid temperature readings do not always have to be local maxima. For example, after identifying the reading 812, the algorithm associated with the process 900 can report a series of readings between $t_4$ and $t_5$ indicated by the curved line 832 as they satisfy Condition 2.

With reference to FIG. 2C, certain aspects of various temperature monitoring algorithms described herein are performed by the processor 202 (FIG. 2C) executing one or more sequences of one or more instructions using threshold limits contained in an internal machine-readable medium such as the internal memory 219 or the memory 210. For example, the processor 202 can determine the loss of body-probe thermal contact by executing instructions contained in the internal memory 202 that involve computation of a rate of decline in temperature readings and comparison of the rate of decline to a threshold rate of decline stored in the memory 210 or generation of a threshold decay curve 841-849 based on a threshold decay rate and comparison of the current $T_{NEW}$ reading to the threshold decay curve. The processor 202 may be a microprocessor, a microcontroller, a digital signal processor (DSP), or an application specific integrated circuit (ASIC) capable of executing computer instructions. Such instructions and/or threshold limits may be read into the memory 219, 210 from another machine-readable medium, such as a CD, flash memory, or a wireless transmission. Execution of the sequences of instructions contained in the memory 219 causes the processor 202 to perform the process steps described herein. One or more processors in a multi-processing arrangement may also be employed to execute the sequences of instructions contained in memory 219. In alternative embodiments, hard-wired circuitry may be used in place of or in combination with software instructions to implement various embodiments. Thus, embodiments are not limited to any specific combination of hardware circuitry and software.

The term "machine-readable medium" as used herein refers to any medium that participates in providing instructions to processor 202 for execution or storing results of or parameters (e.g., variables or constants) for computations such as for the determination of the occurrence and loss of thermal contact between the patient's body and the temperature probe. Such a medium may take many forms, including, but not limited to, non-volatile media, volatile media, and transmission media. Non-volatile media include, for example, optical or magnetic disks, such as data storage device. Volatile media include dynamic memory, such as the memory 210. Transmission media include coaxial cables, copper wire, and fiber optics, including the wires that comprise bus 204. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, a carrier wave, or any other medium from which a computer can read.

In some embodiments, after the processor 202 programmatically generates data such as a sequence of temperature readings or indications of the high temperature condition or the loss of body-probe contact, such values can be either temporarily stored in the machine-readable medium such as the memory 210 until the values are transmitted via the wireless transmitter 209. Instructions and/or various threshold limits (e.g., the threshold rates of rise and decline, the maximum duration for $T_{MAX}$) used by the temperature monitoring scheme of the present disclosure may be downloaded into the memory 210, 219 via wireless transmission from an external device (e.g., the surveillance server 60 via the bridge 40) via the receiver 206.

The foregoing description is provided to enable any person skilled in the art to practice the various embodiments described herein. While the foregoing embodiments have been particularly described with reference to the various figures and embodiments, it should be understood that these are for illustration purposes only and should not be taken as limiting the scope of the claims.

The word "exemplary" is used herein to mean "serving as an example or illustration." Any aspect or design described herein as "exemplary" is not necessarily to be construed as preferred or advantageous over other aspects or designs.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. A temperature probe for measuring a temperature of an axilla of a person, comprising:
   a first adhesive element;
   a temperature sensing portion configured for placement within the axilla;
   a second adhesive element;
   a coiled electrical conductor coupled between the first adhesive element and the temperature sensing portion and having a length sufficient to extend from the temperature sensing portion to a first location outside of the axilla on a first side of the axilla; and
   a spring element coupled between the temperature sensing portion and the second adhesive element and having a length sufficient to extend from the temperature sensing portion to a second location outside of the axilla on an opposing second side of the axilla,
   wherein the coiled electrical conductor and the spring element are configured to cooperate with the first and second adhesive elements to hold the temperature sensing portion within the axilla when the first and second adhesive elements are attached at the first and second locations outside of the axilla.

2. The temperature probe of claim 1, further comprising:
   a monitoring device; and
   a flexible cable coupled between the first adhesive element the monitoring device.

3. The temperature probe of claim 1, further comprising an electrical conductor configured for coupling between a monitoring device and the temperature sensing portion.

4. The temperature probe of claim 3, wherein the monitoring device is a vital-sign monitoring patch.

5. The temperature probe of claim 1, wherein the spring element comprises at least one coiled section acting as a spring.

6. The temperature probe of claim 1, wherein the temperature sensing element comprises a thermocouple.

7. The temperature probe of claim 1, wherein the temperature sensing element comprises a thermistor.

8. The temperature probe of claim 1, wherein the temperature sensing element comprises a resistance temperature detector (RTD), the RTD comprising platinum.

9. A system for monitoring a temperature of a person having an axilla disposed between a chest and a back, the system comprising:
   a first adhesive element;
   a temperature sensing element;
   a second adhesive element;
   a coiled electrical conductor coupled between the first adhesive element and the temperature sensing element;
   a spring element coupled between the temperature sensing element and the second adhesive element; and
   a monitoring patch comprising an adhesive backing for attachment to the person, the monitoring patch configured to receive signals from the temperature sensing element via the coiled electrical conductor, the monitoring device including a wireless communication system to wirelessly transmit readings based on the received signals; and
   wherein the coiled electrical conductor and the spring element each have a sufficient length such that the temperature sensing element is retained in the axilla by the first adhesive element, the second adhesive element, the coiled electrical conductor and the spring element when the first adhesive element is attached to a first point on the person that is external to the axilla on one of the chest and the back of the person and the second adhesive element is attached to a second point on the person that is external to the axilla on the other of the chest and the back of the person.

10. The system of claim 9, wherein the monitoring device is a vital-sign monitor patch, the monitor patch configured to measure body temperature and at least one other vital sign of the person wearing the monitor patch.

11. The system of claim 10, wherein the at least one other vital sign comprises at least one of pulse rate, blood pressure, and respiratory rate.

12. The system of claim 9, further comprising an additional coiled electrical conductor coupled between the monitoring device and the first adhesive element.

13. The system of claim 12 wherein the system is configured to remain attached to the person for a period of time.

14. The system of claim 12, wherein the spring element comprises a coiled section.

15. A method of monitoring a temperature of an axilla of a person, comprising:
- placing a sensing portion of a temperature probe within the axilla of the person,
- attaching a first adhesive element to the person at a first location on the person, wherein the first location is external to the axilla;
- attaching a second adhesive element at a second location on the person, wherein the second location is external to the axilla and on an opposing side of the axilla; and
- retaining the sensing portion within the axilla with a coiled electrical conductor coupled between the first adhesive element and the sensing portion and a spring element coupled between the second adhesive element and the sensing portion.

16. The method of claim 15, further comprising wirelessly transmitting readings representative of sensed body temperatures of the person as determined by a monitoring device based on signals received from the temperature sensing element.

17. The method of claim 16, wherein the monitoring device is a vital-sign monitoring patch, the monitor patch configured to measure body temperature and at least one other vital sign of the person wearing the monitor patch.

18. The method of claim 17, wherein the at least one other vital sign comprises at least one of pulse rate, blood pressure, and respiratory rate.

* * * * *